United States Patent [19]

Wächtler et al.

[11] Patent Number: 5,393,459

[45] Date of Patent: Feb. 28, 1995

[54] OPTICALLY ACTIVE COMPOUNDS, AND A LIQUID-CRYSTALLINE PHASE

[75] Inventors: Andreas Wächtler, Griesheim; Thomas Geelhaar, Mainz; Reinhard Hittich, Modautal; Ekkehard Bartmann, Erzhausen; Joachim Krause, Dieburg; Eike Poetsch, Mühltal, all of Germany

[73] Assignee: Merck Patent Gesellschaft Mit Beschrankter Haftung, Darmstadt, Germany

[21] Appl. No.: 956,938

[22] Filed: Oct. 5, 1992

Related U.S. Application Data

[63] Continuation of Ser. No. 635,177, Jan. 11, 1991, abandoned.

[30] Foreign Application Priority Data

| May 11, 1989 | [DE] | Germany | 3915378 |
| May 13, 1989 | [DE] | Germany | 3915698 |
| Jun. 23, 1989 | [DE] | Germany | 3920571 |
| Jul. 7, 1989 | [DE] | Germany | 3922307 |
| Jul. 7, 1989 | [DE] | Germany | 3922308 |
| Jul. 7, 1989 | [DE] | Germany | 3922416 |
| Jul. 14, 1989 | [DE] | Germany | 3923324 |

[51] Int. Cl.$^6$ ............... C09K 19/30; C09K 19/34; C09K 19/12; G09F 1/13
[52] U.S. Cl. ............... 252/299.63; 252/299.61; 252/299.66; 252/299.67; 544/298; 544/224; 546/339; 548/136; 568/631; 568/647; 359/103
[58] Field of Search ............... 252/299.61, 299.63; 558/425, 431

[56] References Cited

U.S. PATENT DOCUMENTS

| 4,798,680 | 1/1989 | Nohira et al. | 252/299.01 |
| 4,867,903 | 9/1989 | Nohira et al. | 252/299.61 |

(List continued on next page.)

FOREIGN PATENT DOCUMENTS

| 0278665 | 8/1988 | European Pat. Off. |
| 0293910 | 12/1988 | European Pat. Off. |
| 294852 | 12/1988 | European Pat. Off. |
| 0304320 | 2/1989 | European Pat. Off. |
| 8705017 | 12/1987 | WIPO |

Primary Examiner—Robert L. Stoll
Assistant Examiner—C. Harris
Attorney, Agent, or Firm—Millen, White, Zelano & Branigan

[57] ABSTRACT

The invention relates to optically active compounds of the formula I

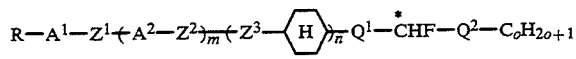

in which

R is an alkyl or alkenyl radical having up to 15 carbon atoms which is unsubstituted, monosubstituted by —CN or at least monosubstituted by fluorine or chlorine, it also being possible for a CH$_2$ group in these radicals to be replaced by —O—, —CO—, —O—CO—, —CO—O— or —O—CO—O—, A$^1$ and A$^2$ are each, independently of one another, a 1,4-phenylene radical, pyridine-2,5-diyl radical, pyrimidine-2,5-diyl radical, pyrazine-2,5-diyl radical, pyridazine-3,6-diyl radical, 1,3,4-thiadiazole-2,5-diyl radical, 1,2,4-thiadiazole-3,5-diyl radical or trans-1,4-cyclohexylene radical, each of which is unsubstituted or substituted by one or two fluorine atoms, and in which, in addition, one or two non-adjacent CH$_2$ groups may be replaced by —O— and/or —S—, and/or a CH group, Z$^1$, Z$^2$ and Z$^3$ are each, independently of one another, —CO—O—, —O—CO—, —CH$_2$O—, —OCH$_2$—, —CH$_2$CH$_2$—, —CH=CH—, —C≡C— or a single bond, Q$^1$ is —CH$_2$CH$_2$—, —CH$_2$CH$_2$CH$_2$—, —OCH$_2$—, —CH$_2$OCH$_2$—, —OCH$_2$CH$_2$—, —O—CO— or —CO—OCH$_2$—, Q$^2$ is —O—, —O—CO—, —(CH$_2$)$_3$—)— or a single bond, m is 0, 1, 2 or 3, n is 0 or 1, and o is 1 to 9, and the use thereof as components of liquid-crystalline phases.

3 Claims, No Drawings

U.S. PATENT DOCUMENTS

| | | | |
|---|---|---|---|
| 4,904,410 | 2/1990 | Nohira et al. | 252/299.61 |
| 4,906,402 | 3/1990 | Jackson et al. | 252/299.65 |
| 4,917,817 | 4/1990 | Nohira et al. | 252/299.01 |
| 4,917,821 | 4/1990 | Mori et al. | 252/299.63 |
| 4,918,213 | 4/1990 | Nohira et al. | 558/271 |
| 4,921,632 | 5/1990 | Nakamura et al. | 252/299.61 |
| 4,985,583 | 1/1991 | Eidenschink et al. | 558/431 |
| 4,986,631 | 1/1991 | Eidenschink et al. | 252/299.63 |
| 5,108,652 | 4/1992 | Eidenschink et al. | 252/299.63 |

OPTICALLY ACTIVE COMPOUNDS, AND A LIQUID-CRYSTALLINE PHASE

This application is a continuation of application Ser. No. 07/635,177, filed Jan. 11, 1991, abandoned.

The invention relates to optically active compounds of the formula I

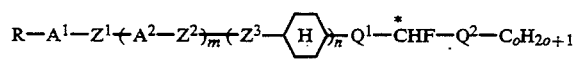

$$R-A^1-Z^1(A^2-Z^2)_m(Z^3-\langle H \rangle)_n Q^1-\overset{*}{C}HF-Q^2-C_oH_{2o+1}$$

in which
R is an alkyl or alkenyl radical having up to 15 carbon atoms which is unsubstituted, monosubstituted by —CN or at least monosubstituted by fluorine or chlorine, it also being possible for a $CH_2$ group in these radicals to be replaced by —O—, —CO—, —O—CO—, —CO—O— or —O—CO—O—, $A^1$ and $A^2$ are each, independently of one another, a 1,4-phenylene radical, pyridine-2,5-diyl radical, pyrimidine-2,5-diyl radical, pyrazine-2,5-diyl radical, pyridazine-3,6-diyl radical, 1,3,4-thiadiazole-2,5-diyl-radical, 1,2,4-thiadiazole-3,5-diyl radical or trans-1,4-cyclohexylene radical, each of which is unsubstituted or substituted by one or two fluorine atoms, and in which, in addition, one or two non-adjacent $CH_2$ groups may be replaced by —O— and/or —S—, and/or a CH group, $Z^1$, $Z^2$ and $Z^3$ are each, independently of one another, —CO—O—, —O—CO—, —$CH_2$O—, —O$CH_2$—, —$CH_2CH_2$—, —CH=CH—, —C≡C— or a single bond, $Q^1$ is —$CH_2CH_2$—, —$CH_2CH_2CH_2$—, —O$CH_2$—, —$CH_2$O$CH_2$—, —O$CH_2CH_2$—, —O—CO— or —CO—O$CH_2$—, $Q^2$ is —O—, —O—CO—, —$(CH_2)_3$—O— or a single bond, m is 0, 1, 2 or 3,
n is 0 or 1, and
o is 1 to 9.

Like similar compounds described in German Offenlegungsschrift 3,515,373, the compounds of the formula I can be used as components of chiral tilted smectic liquid-crystalline phases.

Chiral tilted smectic liquid-crystalline phases having ferroelectric properties can be prepared by adding a suitable chiral dope to base mixtures having one or more tilted smectic phases (L. A. Beresnev et al., Mol. Cryst. Liq. Cryst. 89, 327 (1982); H. R. Brand et al., J. Physique 44., (lett.), L-771 (1983). Phases of this type can be used as dielectrics for rapidly switching displays based on the principle of SSFLC technology described by Clark and Lagerwall (N. A. Clark and S. T. Lagerwall, Appl. Phys. Lett. 36, 899 (1980); U.S. Pat. No. 4,367,924) on the basis of the ferroelectric properties of the chiral tilted phase. In this phase, the long molecules are arranged in layers, the molecules having a tilt angle to the layer perpendiculars. On moving from layer to layer, the tilt direction changes by a small angle with respect to an axis perpendicular to the layers, thus forming a helical structure. In displays based on the principle of SSFLC technology, the smectic layers are arranged perpendicular to the plates of the cell. The helical arrangement of the tilt directions of the molecules is suppressed by a very small separation of the plates (about 1-2 μm). The longitudinal axes of the molecules are therefore forced to arrange themselves in a plane parallel to the plates of the cell, thus causing two preferred tilt orientations. By applying a suitable electrical alternating field, it is possible to switch back and forth between these two states in the liquid-crystalline phase exhibiting spontaneous polarization. This switching process is considerably faster than in customary twisted cells (TN-LCDs) based on nematic liquid crystals.

It is a great disadvantage for many applications of the currently available materials having chiral tilted smectic phases (such as, for example, Sc*) that they have a relatively high optical anisotropy and unacceptably short switching times, due to relatively high viscosity values, and that the dielectric anisotropy values are greater than zero or, if they are negative, have values only slightly different from zero. Negative values for the dielectric anisotropy are necessary if the planar orientation necessary is caused by superimposing the control field with an AC holding field of small amplitude (J. M. Geary, SID Congress, Orlando/Fla., April/May 1985, Paper 8.3).

It has now been found that the use of compounds of the formula I as components of chiral tilted smectic mixtures can significantly reduce the disadvantages mentioned. The compounds of the formula I are thus pre-eminently suitable as components of chiral tilted smectic liquid-crystalline phases. In particular, they can be used to prepare chiral tilted smectic liquid-crystalline phases which are particularly stable chemically and have favorable ferroelectric phase ranges, in particular broad Sc* phase ranges, negative or positive dielectric anisotropy, low optical anisotropy, a favorable pitch level, low viscosity and values for spontaneous polarization which are high for phases of this type, and very short switching times. P is the spontaneous polarization in $nC/cm^2$.

In addition, the provision of the compounds of the formula I very generally considerably broadens the range of liquid-crystalline substances which are suitable, from various applicational points of view, for the preparation of ferroelectric mixtures.

The compounds of the formula I have a broad range of applications. Depending on the choice of substituents, these compounds can be used as base materials of which liquid-crystalline phases are predominantly composed; however, it is also possible to add compounds of the formula I to liquid-crystalline base materials from other classes of compound, in order, for example, to vary the dielectric and/or optical anisotropy and/or the spontaneous polarization and/or the phase range and/or the tilt angle and/or the pitch and/or the switching times of a phase of this type. The compounds of the formula I are furthermore suitable as intermediates in the preparation of other substances which can be used as constituents of liquid-crystalline phases.

In the pure state, the compounds of the formula I are colorless and have favorable optical anisotropy values. Some of the compounds of the formula I exhibit liquid-crystalline mesophases in a temperature range which is in a favorable position for electrooptical use, but isotropic or monotropically liquid-crystalline compounds of the formula I can also be employed advantageously as components of chiral tilted smectic phases. They are very stable chemically, thermally and to light.

The invention thus relates to the compounds of the formula I, and to the use of the compounds of the formula I as components of liquid-crystalline phases.

The invention also relates to chiral tilted smectic liquid-crystalline phases containing at least one compound of the formula I and at least one carbon atom linked to four different substituents.

The invention furthermore relates to phases of this type containing at least one compound of the formula I and to liquid-crystal display elements, in particular electrooptical display elements, which contain phases of this type.

For reasons of simplicity, Ph below is a 1,4-phenylene group in which, in addition, one or two CH groups may be replaced by N, Cy is a 1,4-cyclohexylene group in which, in addition, one or two non-adjacent $CH_2$ groups may be replaced by O atoms, Dio is a 1,3-dioxane-2,5-diyl group, Tia is a 1,3,4-thiadiazole-2,5-diyl group, and Bi is a bicyclo(2,2,2)octylene group.

Above and below, R, $A^1$, $Z^1$, $A^2$, $Z^2$, m, X, $Z^3$, n, Q, o and $Q^2$ have the meaning indicated, unless expressly stated otherwise.

In the preferred compounds of the formulae above and below, the alkyl radicals, in which, in addition, one $CH_2$ group (alkoxy or oxaalkyl) may be replaced by an O atom, may be straight-chain or branched. They preferably have 5, 6, 7, 8, 9 or 10 carbon atoms and accordingly are preferably pentyl, hexyl, heptyl, octyl, nonyl, decyl, pentoxy, hexoxy, heptoxy, octoxy, nonoxy or decoxy, furthermore also ethyl, propyl, butyl, undecyl, dodecyl, propoxy, ethoxy, butoxy, undecoxy, dodecoxy, 2-oxapropyl (=2-methoxymethyl), 2-(=ethoxymethyl) or 3-oxabutyl (=2-methoxypentyl), 2-, 3- or 4-oxapentyl, 2-, 3-, 4- or 5-oxahexyl, or 2-, 3-, 4-, 5- or 6-oxaheptyl.

$A^1$ and $A^2$ are preferably Cy or Ph. In the compounds of the formulae above and below, Ph is preferably a 1,4-phenylene (Phe), a pyrimidine-2,5-diyl (Pyr), a pyridine-2,5-diyl (Pyn), a pyrazine-3,6-diyl or a pyridazine-2,5-diyl group, particularly preferably Phe, Pyr or Pyn. The compounds according to the invention preferably contain not more than one 1,4-phenylene group in which one or two CH groups are replaced by N. Cy is preferably a 1,4-cyclohexylene group. However, particularly preferred compounds of the formula I are those in which one of the groups $A^2$ is a 1,4-cyclohexylene group which is substituted in the 1- or 4-position by CN and in which the nitrile group is in the axial position, i.e. group $A^2$ has the following configuration:

Particularly preferred compounds of the formula I and of the sub-formulae above are those which contain a —Ph—Ph— group. —Ph—Ph— is preferably —Phe—Phe—, Phe—Pyr or Phe—Pyn. Particularly preferred groups are

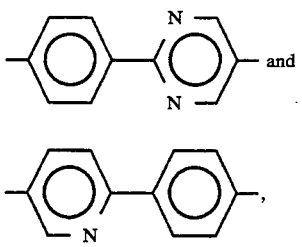

and furthermore 4,4'-biphenylyl which is unsubstituted or monosubstituted or polysubstituted by fluorine.

$Z^1$ is preferably a single bond, and secondarily preferably an —O—CO—, —CO—O—, —C≡C— or —$CH_2CH_2$— group.

$Z^1$ is particularly preferably —CO—O, —O—CO—, —C≡C— or —$CH_2CH_2$—, in particular the —$CH_2CH_2$— and the —C≡C— group.

Compounds of the formulae above and below having branched wing groups R may be important. Branched groups of this type generally contain not more than two chain branches. R is preferably a straight-chain group or a branched group having not more than one chain branch.

Preferred branched radicals are isopropyl, 2-butyl (=1-methylpropyl), isobutyl (=2-methylpropyl), tert.-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

Of the compounds of the formula I, those are preferred in which at least one of the radicals present therein has one of the preferred meanings indicated.

Those of the abovementioned formulae which contain one or more groups Dio, Dit, Pip and/or Pyr in each case include the two possible 2,5-(Dio, Dit, Pyr) or 1,4-positional isomers (Pip).

Preferred compounds of the formula I are the optically active compounds of the formula IV

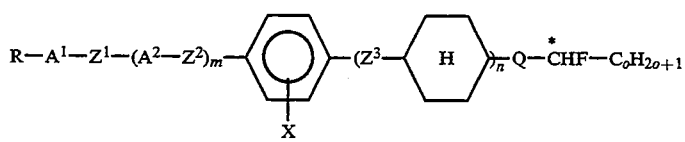

IV in which

R is an alkyl or alkenyl radical having up to 15 carbon atoms which is unsubstituted, monosubstituted by —CN or at least monosubstituted by fluorine or chlorine, it also being possible for one $CH_2$ group in these radicals to be replaced by —O—, —CO—, —O—CO—, —CO—O— or —O—CO—O—, $A^1$ and $A^2$ are each, independently of one another, a 1,4-phenylene radical, pyridine-2,5-diyl radical, pyrimidine-2,5-diyl radical, pyrazine-2,5-diyl radical, pyridazine-3,6-diyl radical, 1,3,4-thiadiazole-2,5-diyl-radical, 1,2,4-thiadiazole-3,5-diyl radical or trans-1,4-cyclohexylene radical, each of which is unsubstituted or substituted by one or two fluorine atoms, and in which, in addition, one or two non-adjacent $CH_2$ groups may be replaced by —O— —S—, and/or one CH group may be replaced by —C(CN)—, or are a 1,4-cyclohexenylene radical, 1,4-bicyclo(2.2.2)octylene radical or a piperidine-1,4-diyl radical, $Z^1$, $Z^2$ and $Z^3$ are each, independently of one another, —CO—O—, —O—CO—, —CH$_2$O—, —OCH$_2$—, —CH$_2$CH$_2$—, —CH=CH—, —C≡C— or a single bond, X is H or F, Q is —OCH$_2$, —COOCH$_2$— or —CH$_2$OCH$_2$—, o is 1 to 12, and one of the two values m and n is 0 and the other is 0 or 1, with the provisos that, in the case where Q=—OCH$_1$— or —COOCH$_2$—, (a) n=1 and m=0, (b) one of the rings $A^1$ and $A^2$ is 1,3,4-thiadiazole-2,5-diyl, 1,2,4-thiadiazole-3,5-diyl, trans-1,4-cyclohexylene in which one or two non-adjacent CH$_2$ groups have been replaced by —O— and/or —S— and/or one CH group has been replaced by —C(CN)—, or is 1,4-cyclohexenylene, 1,4-bicyclo(2.2.2)octylene, piperidine-1,4-diyl or 2,3-difluoro-1,4-phenylene, (c) n=0 and $Z^1$ and/or $Z^2$ is —O—CO—, —CH$_2$O—, —CH$_2$O—, —CH$_2$CH$_2$—, —CH=CH— or —C≡C—, or (d) R is an alkyl or alkenyl radical having up to 15 carbon atoms which is monosubstituted by —CN or at least monosubstituted by fluorine or chlorine, it also being possible for one CH$_2$ group in these radicals to be replaced by —O—, —CO—, —O—CO—, —CO—O— or —O—CO—O—, or is an unsubstituted alkenyl radical having up to 15 carbon atoms, it also being possible for one CH$_2$group in this radical to be replaced by —O—, —CO—, —O—CO—, —CO—O— or —O—CO—O—.

Particular preference is given to the compounds of the formulae IVa to IVe

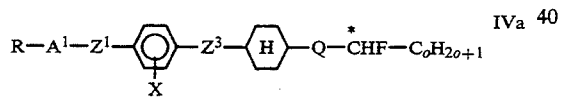   IVa

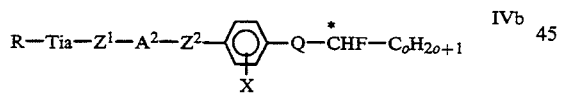   IVb

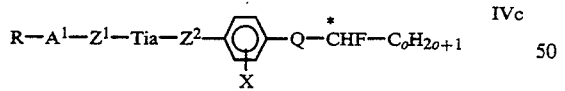   IVc

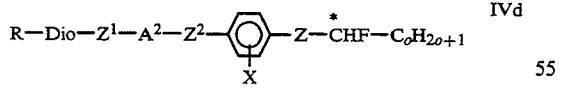   IVd

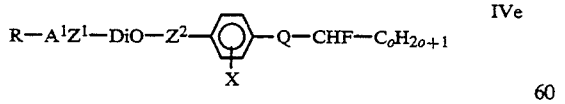   IVe

Further preferred compounds of the formula I are chiral or achiral ring compounds of the formula V

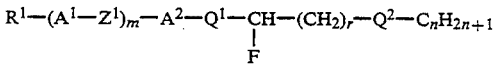

in which $R^1$ is an alkyl or perfluoroalkyl group, in each case having 1-12 carbon atoms and in which, in addition, one or two non-adjacent CH$_2$ or CF$_2$ groups may be replaced by O atoms and/or —CO— groups and/or —CO—O— groups and/or —CH=CH— groups and/or —CHhalogen- and/or —CHCN— groups and/or —O—CO—CHhalogen- and/or —CO—O—CHCN—groups, $A^1$ and $A^2$ are each, independently of one another, 1,4-phenylene which is unsubstituted or substituted by one or two F and/or Cl atoms and/or CH$_3$ groups and/or CN groups, and in which, in addition, one or two CH groups may be replaced by N, are 1,4-cyclohexylene in which, in addition, one or two non-adjacent CH$_2$ groups may be replaced by O atoms and/or S atoms, or are piperidine-1,4-diyl, 1,4-bicyclo(2,2,2)octylene, 1,3,4-thiadiazole-2,5-diyl, naphthalene-2,6-diyl, decahydronaphthalene-2,6-diyl or 1,2,3,4-tetrahydronaphthalene-2,6-diyl, $Z^1$ is —CO—O—, —O—CO—, —CH$_2$CH$_2$—, —OCH$_2$—, —CH$_2$O—, —C≡C— or a single bond, m is 1, 2 or 3, n is 1 to 7, r is 1 or 2, $Q^1$ is —O—CH$_2$—, —O—CO— or, in the case where $A^1$—$Z^1$—$A^2$=

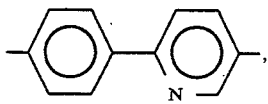

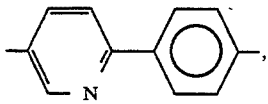

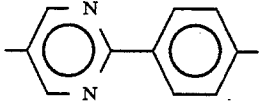

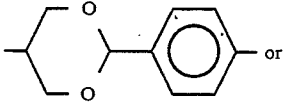

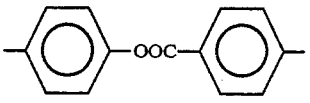

is alternatively —CH$_2$CH$_2$—, and $Q^2$ is —O— or —O—CO—.

Particularly preferred compounds of the formula V are those of the formulae V1 to V6

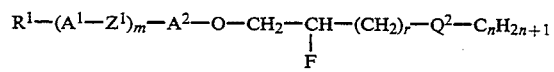   V1

-continued

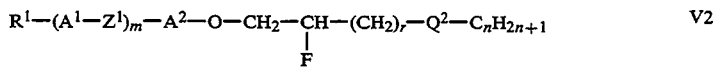 V2

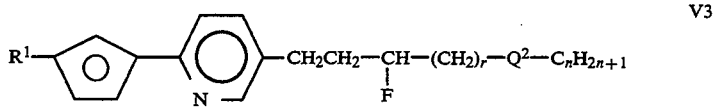 V3

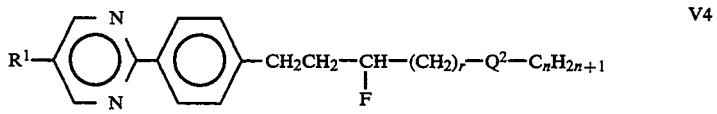 V4

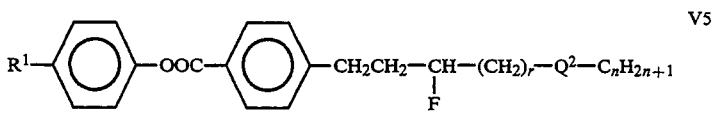 V5

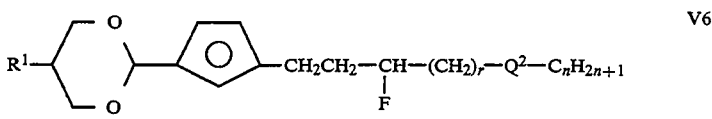 V6

Above and below, $R^1$, $A^1$, $Z^1$, $A^2$, m, n, $Q^1$ and $Q^2$ are as defined for the formula V, unless expressly stated otherwise.

The radical $-Q^1-CHF-(CH_2)_r-Q^2-C_nH_{2n+1}$ is referred to as R* below.

The compounds of the formula V accordingly include, in particular, compounds of the sub-formulae Va (having two rings)

$R^1-A^1-Z^1-A^2-R*$  Va

Vb (having three rings):

$R^1-(A^1-Z^1)_2-A^2-R*$  Vb and Vc (having four rings):

$R^1-(A^1-Z^1)_3-A^2-R*$  Vc

Of these, those of the formulae Va and Vb are particularly preferred.

The preferred compounds of the formula Va include those of the sub-formulae Va1 to Va4:

$R^1-Ph-Z^1-Ph-R*$  Va1

$R^1-Ph-Z^1-Cy-R*$  Va2

$R^1-Cy-Z^1-Ph-R*$  Va3

$R^1-Cy-Z^1-Cy-R*$  Va4

Of these, those of the sub-formula Va1 are particularly preferred.

The preferred compounds of the formula Vb include those of the sub-formulae Vb1 to Vb8:

$R^1-Ph-Z^1-Ph-Z^1-Ph-R*$  Vb1

$R^1-Ph-Z^1-Ph-Z^1-Cy-R*$  Vb2

$R^1-Cy-Z^1-Ph-Z^1-Cy-R*$  Vb3

$R^1-Ph-Z^1-Cy-Z^1-Ph-R*$  Vb4

$R^1-Ph-Z^1-Cy-Z^1-Cy-R*$  Vb4

$R^1-Cy-Z^1-Cy-Z^1-Ph-R*$  Vb6

$R^1-Cy-Z^1-Ph-Z^1-Cy-R*$  Vb7

$R^1-Cy-Z^1-Cy-Z^1-Cy-R*$  Vb8

Further preferred compounds of the formula IV are the 2,5-disubstituted heterocyclic compound of the formula VI

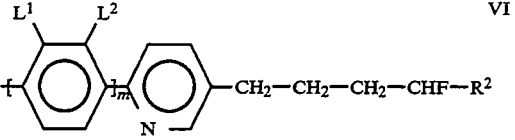 VI in which
$R^1$ is alkyl, alkenyl or oxaalkyl having up to 12 carbon atoms,
$R^2$ is alkyl having 2 to 12 carbon atoms,
$L^1$ and $L^2$ are each, independently of one another, H or F,
Y is $-O-$, $-CO-O-$, $-O-CO-$ or a single bond, and
m is 1 or 2.

Above and below, $R^1$, $R^2$, m, $L^1$, $L^2$ and Y are as defined for the formula VI, unless expressly stated otherwise.

The compounds of the formula VI accordingly include, in particular, compounds of the sub-formulae VIa and VIb:

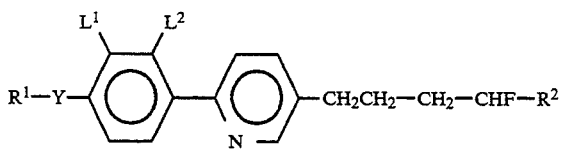 VIa

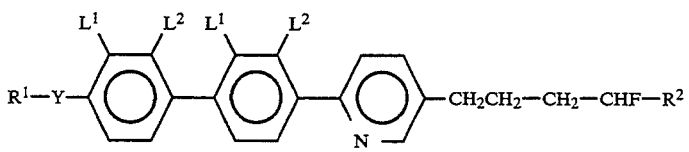 VIb

Of these, those of the formula VIa are particularly preferred.

Y is preferably —O— or —CO—O—, particularly preferably —O—.

m is preferably 1.

The radical

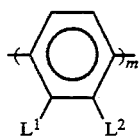

preferably has one of the meanings 1 to 6 below:

1 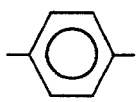

2 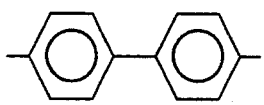

3 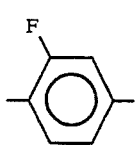

4 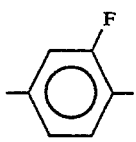

5, 6 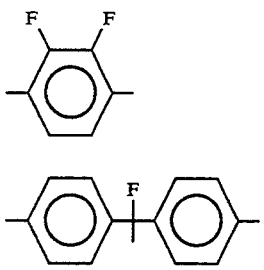

Meanings 1 and 2, in particular 1, are particularly preferred. In 6, the fluorine can be in any position.

The compounds of the formula VI are preferably optically active and are used as chiral dopes for ferroelectric mixtures. —CHF— is preferably an asymmetric carbon atom.

$R^2$ is preferably straight-chain or branched alkyl having up to 10 carbon atoms, preferably 3 to 8 carbon atoms.

Further preferred compounds of the formula I are chiral or achiral ring compounds of the formula VII

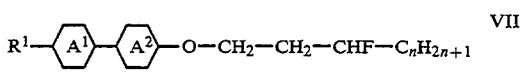 VII in which $R^1$ is an alkyl or perfluoroalkyl group, in each case having 1–12 carbon atoms and in which, in addition, one or two non-adjacent $CH_2$ or $CF_2$ groups may be replaced by O atoms and/or —CO— groups and/or —CO—O— groups and/or —CH=CH— groups and/or —CHhalogen- and/or —CHCN— groups and/or —O—CO—CHhalogen- and/or —CO—O—CHCN— groups, $A^1$ and $A^2$ are each, independently of one another, 1,4-phenylene which is unsubstituted or substituted by one or two F atoms and in which, in addition, one or two CH groups may be replaced by N, and n is 1 to 12.

Above and below, $R^1$, $A^1$, $A^2$ and n are as defined for the formula VII, unless expressly stated otherwise.

The radical —O—$CH_2$—$CH_2CHF$—$C_nH_{2n+1}$ is referred to as R* below.

The compounds of the formula VII accordingly include, in particular, the preferred compounds of the sub-formulae VIIa to VIIf:

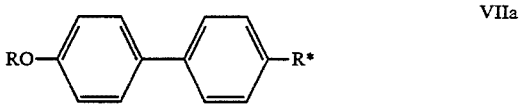 VIIa

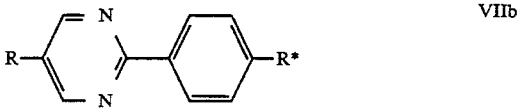 VIIb

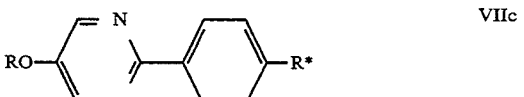 VIIc

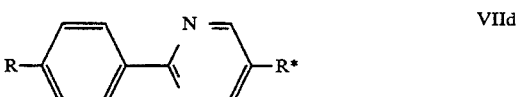 VIId

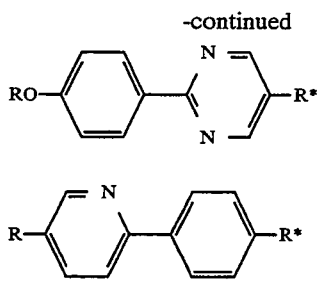

Of these, those of the formulae VIIb, VIIc and VIIe are particularly preferred.

A¹ and A² are preferably each, independently of one another, a 1,4-phenylene (Phe), a pyrimidine-2,5-diyl (Pyr), a pyridine-2,5-diyl (Pyn), a pyrazine-3,6-diyl or a pyridazine-2,5-diyl group, particularly preferably Phe, Pyr or Pyn. The compounds according to the invention preferably contain not more than one 1,4-phenylene group in which one or two CH groups have been replaced by N.

Particular preference is given to compounds of the formula VII and the above sub-formulae which contain a -Phe-Phe-, Phe-Pyr or Phe-Pyn group. Particular preference is given to the groups

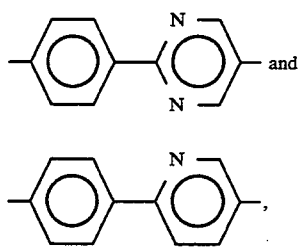

it also being possible for the 1,4-phenylene rings to be substituted by one or two fluorine atoms, and, furthermore, 4,4'-biphenylyl which is unsubstituted or monosubstituted or polysubstituted by fluorine.

The compounds of the formula I are prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for reactions mentioned. Use may also be made here of variants which are known per se, but are not described here in greater detail.

If desired, the starting materials can also be formed in situ by not isolating them from the reaction mixture, but instead immediately reacting them further to form the compounds of the formula I.

The optically active compounds of the formula I are obtained by using corresponding optically active starting materials and/or by chromatographic separation of the optical antipodes by known methods.

Thus, precursors which are suitable for the preparation of compounds of the formula V where r=2 can be prepared from optically active malic acid in accordance with the following reaction scheme (ta/1-3):

As far as this step, the synthesis has been described by Mori et al. (K. Mori, T. Takigawa and T. Matsuo, Tetrahedron 35, 933-944 (1979).

Meyers and Lawsson later found that the chemical purity of the acetonide obtained by this route is only about 90% (A. I. Meyers and J. P. Lawson, THL 23 4883-4886 (1982).

This notwithstanding, the free alcohol group of the acetonide can be etherified by one of the customary methods (for example C. A. Brown and D. Barton, Synthesis (1974) 434, or B. R. Jursic, Tetrahedron 44, 6677-6680 (1988).

The benzyl ether (K. Isaac and P. Kocienski, J. Chem. Soc., Chem. Commun. (1982) 460-462) is a particularly suitable protecting group since it can later easily be removed hydrogenolytically. After the etherification, the isopropylidene ketal is hydrolyzed to the 1,2-diol under standard conditions, and the latter is then converted into the corresponding epoxide under the reaction conditions of Di Fabio and Misiti (R. Di Fabio and D. Misiti, Gazetta Chimica Italiana 118, 209-210 (1988).

Treatment of the acetonide with HBr/glacial acetic acid and subsequent reaction of the bromooxalkyl acetates obtained in this way with K pentoxide also gives the desired epoxides according to the paper by U.

Schmidt et al. (U. Schmidt, J. Tabiersky, F. Bartowiak and J. Wild, Angew. Chem. 92, 201–202 (1980)).

Scheme 2

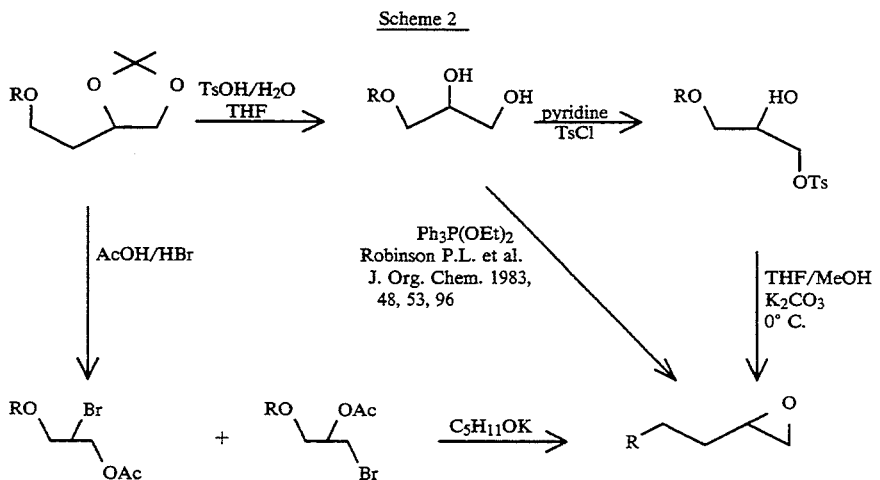

Opening the epoxide using pyridine/HF (N. Mongelli, F. Animati et al., Synthesis 310 (1988)) gives the corresponding fluoroalcohol, which can then be converted into the corresponding tosylate. Such tosylates are particularly suitable for alkylating phenols.

Scheme 3

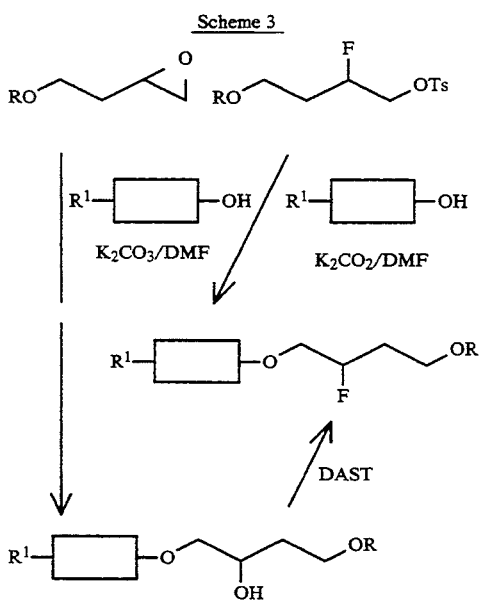

As the above reaction scheme shows, the epoxide can also be reacted directly with phenols. The epoxide is opened with high selectivity on the less-substituted carbon atom to give the chiral secondary alcohol, which is then finally converted into the compounds according to the invention using DAST with inversion. With respect to the conventional reactions of alcohols with DAST, see: M. Hudlicky, Organic Reactions 35 513–637 (1987).

The compounds of the formula V according to the invention where $Q^2$=—O—CO— can be prepared from the corresponding benzyl ethers by hydrogenolysis and subsequent esterification. The preparation is described by the following synthesis scheme:

Scheme 4

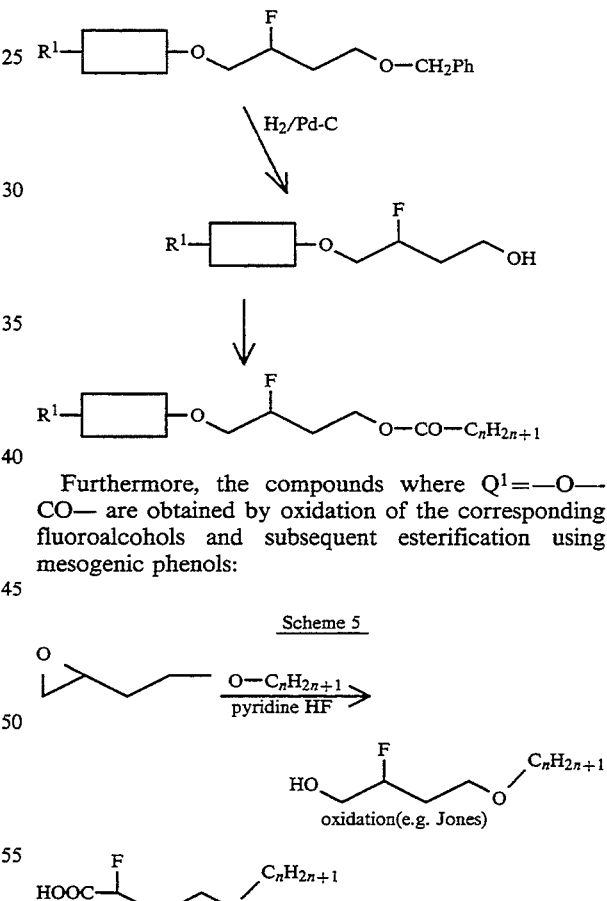

Furthermore, the compounds where $Q^1$=—O—CO— are obtained by oxidation of the corresponding fluoroalcohols and subsequent esterification using mesogenic phenols:

Scheme 5

If racemization occurs during the oxidation, the optically active fluoroacids can be isolated by resolving the racemate by the method of Helmchen (Angew. Chem. 91, 65 (1979)).

CH-acidic compounds, such as, for example, tolunitrile or methylpyridines, likewise open the epoxide in the presence of suitable bases to give the optically active secondary alcohol, which is then fluorinated using DAST with inversion. The following schemes (6–9) show preferred reaction routes.

Scheme 6

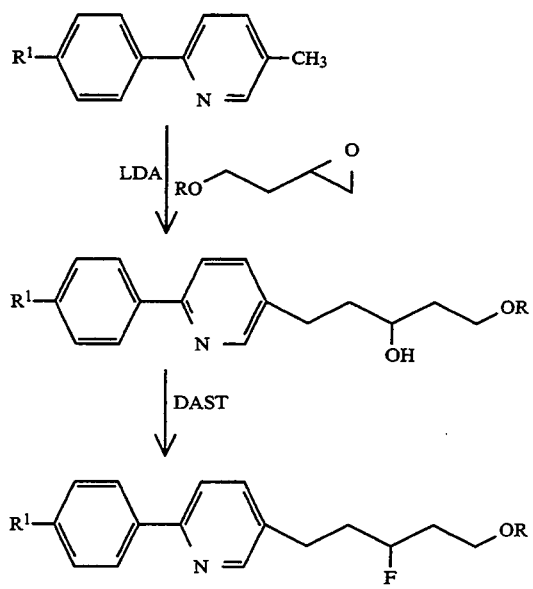

Scheme 7

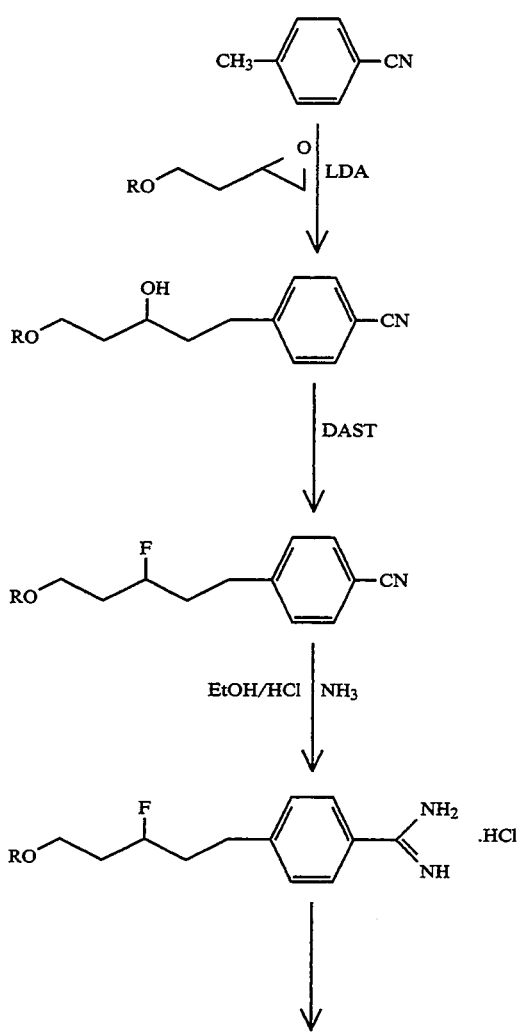

-continued
Scheme 7

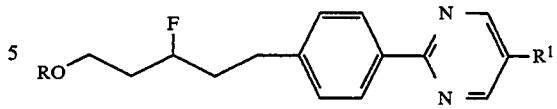

Mild hydrolysis of the nitriles gives, via the imino ethers, according to Pinner, the corresponding benzoic acids:

Scheme 8

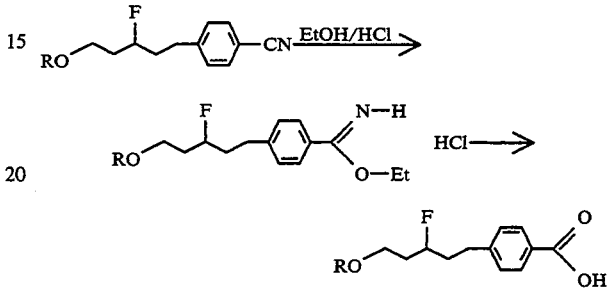

These acids can be esterified by means of hydroxyl groups of typical liquid-crystal components.

The compounds of the formula I where $r=1$ can be prepared analogously using the known epoxides of the formula

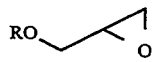

or the fluoroalcohols of the formula

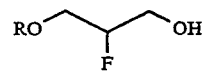

which are obtainable from the latter by customary methods.

The synthesis of the preferred phenylpyridines is described in greater detail below:

Scheme 9

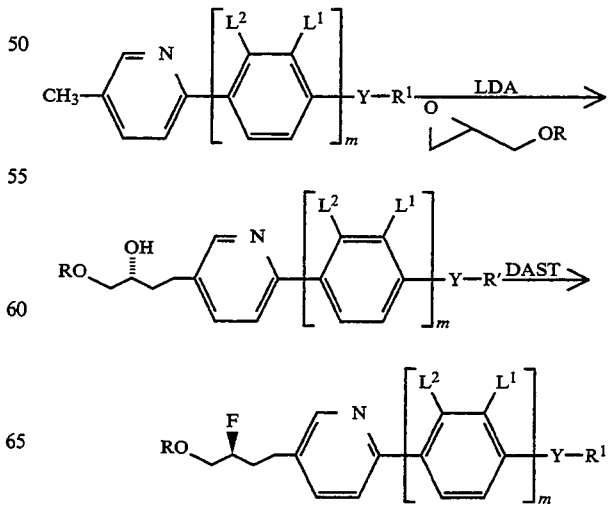

In the formulae above, R is in each case $C_nH_{2n-1}$ (n=1 to 7) and

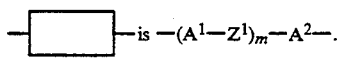 is $-(A^1-Z^1)_m-A^2-$.

Thus, the compounds of the formula VI or precursors which are suitable for their preparation can be prepared by reacting a compound of the formula VI'

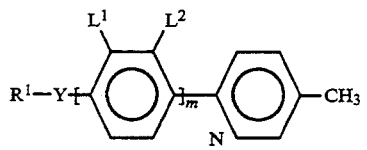 VI' in which $R^1$, Y, $L^2$, $L^2$ and m are as defined above, or a suitable precursor with a compound of the formula VI''

$R^2-CHF-CH_2-CH_2-Hal$    VI'' in which $R^2$ is as defined above, and Hal is preferably Br or I, under basic conditions.

To prepare compounds of the formula VI'', suitable precursors for the epoxide prepared according to Scheme 1 and 2 from optically active malic acid can be prepared in accordance with the following reaction scheme (10):

Scheme 10

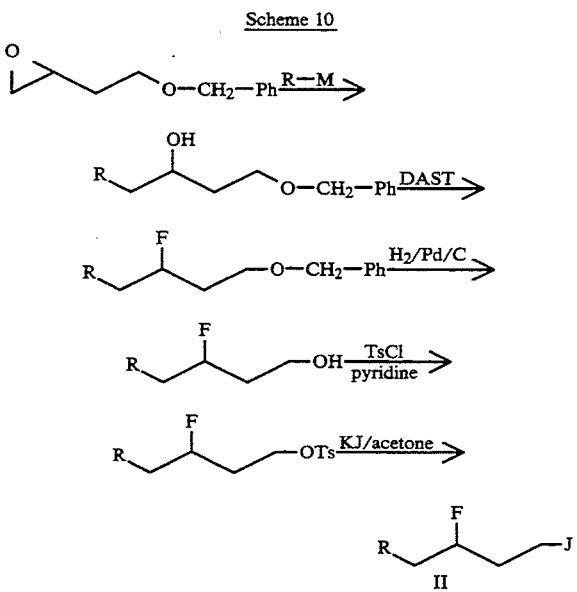

Reaction of the epoxide with organometallic compounds, preferably with Grignard compounds, with ring opening on the less-substituted carbon atom of the epoxide gives, in high selectivity, the corresponding alcohol, which is fluorinated using DAST under standard conditions. Hydrogenolysis finally gives the primary alcohol, whose reactive derivatives VI'' are accessible by standard methods.

The reaction conditions for the reaction of VI' with VI'' are not crucial per se. The 2-substituted 5-methyl-pyridines of the formula VI' are metallated under the conditions given in DE 36 32 411 (Example 3) (it being possible to omit the use of DMPU), and an equimolar amount of an optionally chiral halide of the formula VI'' is then added at $-10°$ C.

The starting materials of the formula VI' are obtainable, for example, from 2-p-methoxyphenyl-5-methyl pyridine by basic ether cleavage using K tert.-butylate in N-methylpyrrolidone (NMP) at 150°–200° C., and subsequent re-etherification using the appropriate alkyl halides or by cross-coupling of the appropriate aromatic boric acids with 2-bromo-5-methylpyridine by the method of M. J. Sharp, W. Cheng and V. Snieckus, Tetrahedron Letters 28., 5093 (1987).

The chiral compounds of the formula I in which $Q^1$ is $-O-CH_2-$ or $CH_2CH_2$, and $Q^2$ is $(CH_2)_3-O-$ are particularly preferred. They can be prepared in accordance with Scheme 11 from chiral epoxides of the

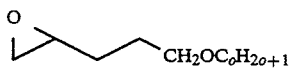

type by ring opening using phenoxides or CH-acidic compounds. The corresponding 4-hydroxymethyl-γ-butyrolacetone is described (II Farmaco 44 (3), 303–313, 1989).

Scheme 11

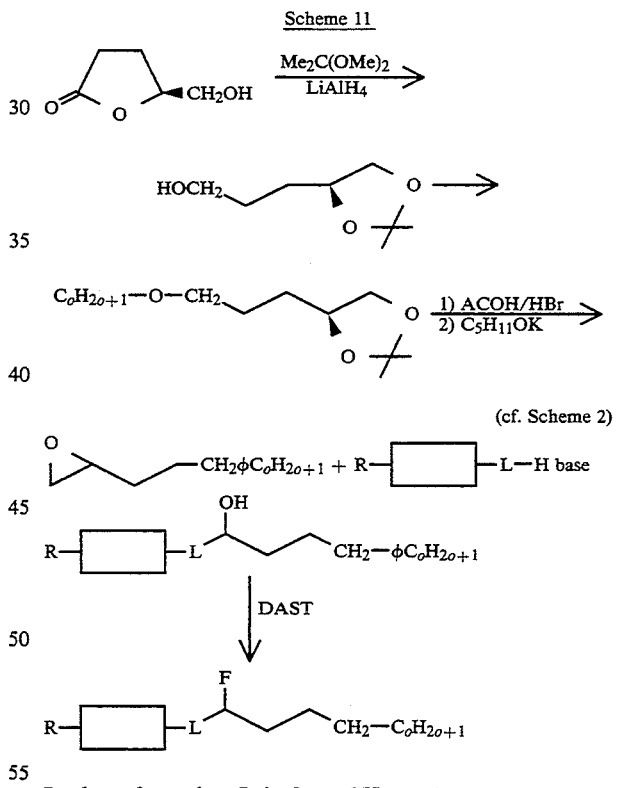

In these formulae: L is O or $CH_2$, and

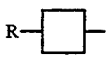

is $R-A^1-Z^1-(A^2-Z^2)_m-(Z^3-H-)_n$

The phases according to the invention contain at least one, preferably at least two, compounds of the formula I. Particular preference is given to chiral tilted smectic liquid-crystalline phases according to the invention whose achiral base mixture contains, in addition to compounds of the formula I, at least one other component having negative or low positive dielectric anisotropy. The chirality is preferably based in part or in full on chiral compounds of the formula I. These phases preferably contain one or two chiral compounds of the formula I. However, it is also possible to use achiral compounds of the formula I (for example in the form of a racemate), in which case the chirality of the phase is caused by other optically active compounds. If chiral compounds of the formula I are used, mixtures having an enantiomeric excess are also suitable in addition to the pure optical antipodes. The other component(s) mentioned above of the achiral base mixture can make up 1 to 50%, preferably 10 to 25%, of the base mixture. Suitable further components having a low positive or negative dielectric anisotropy are compounds of the sub-formulae VIIIa to VIIIp:

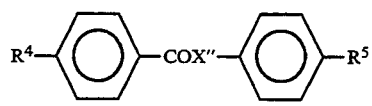 VIIIa

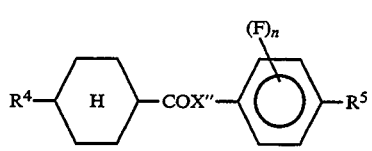 VIIIb

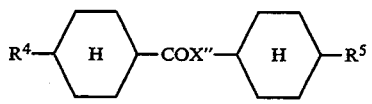 VIIIc

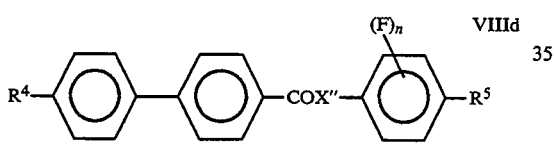 VIIId

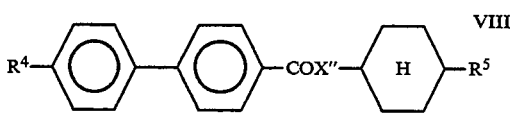 VIIIe

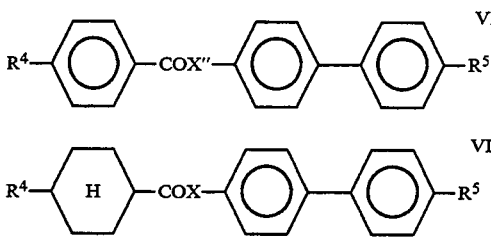 VIIIf

VIIIg

VIIIh

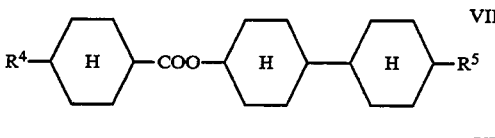 VIIIi

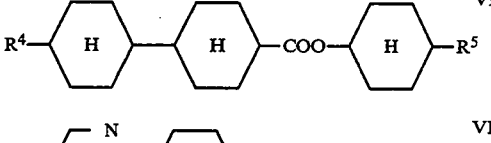

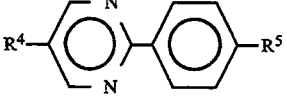 VIIIj

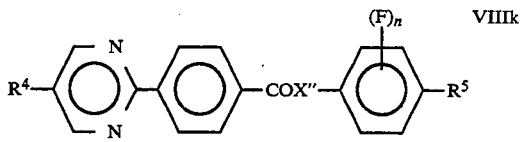 VIIIk

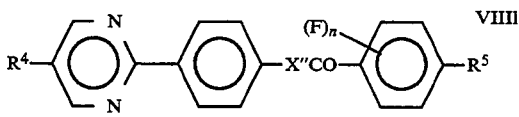 VIIIl

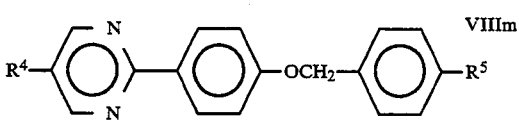 VIIIm

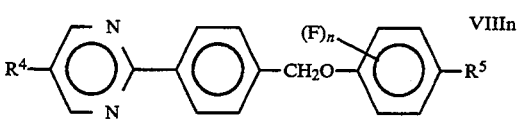 VIIIn

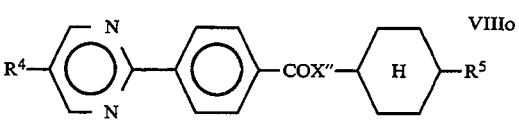 VIIIo

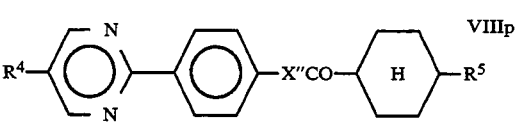 VIIIp $R^4$ and $R^5$ are each preferably straight-chain or branched alkyl, alkoxy, alkanoyloxy or alkoxycarbonyl, in each case having 3 to 12 carbon atoms. X″ is O or S, preferably O. n is 0 or 1.

Particular preference is given to the compounds of the sub-formulae VIIIa, VIIIb, VIIId and VIIIf in which $R^4$ and $R^5$ are each straight-chain alkyl or alkoxy, in each case having 5 to 10 carbon atoms.

The compounds of the sub-formulae VIIIc, VIIIh and VIIIi are suitable as additives for reducing the melting point, and are normally added to the base mixtures in an amount of not more than 5%, preferably 1 to 3%. $R^4$ and $R^5$ in the compounds of the sub-formulae VIIIc, VIIIh and VIIIi are preferably straight-chain alkyl having 2 to 7, preferably 3 to 5, carbon atoms. A further class of compounds which is suitable for reducing the melting point in the phases according to the invention is that of the formula

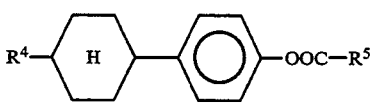

in which $R^4$ and $R^5$ have the preferred meaning given for VIIIc, VIIIh and VIIIi.

As further components having negative dielectric anisotropy, suitable compounds are also those containing the structural element M, N or O.

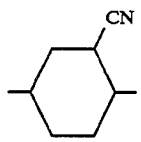

M

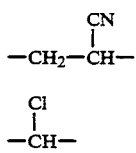

N

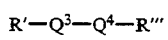

O

Preferred compounds of this type conform to the formulae IXb and IXc:

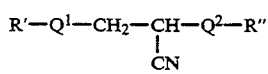

R' and R" are in each case preferably straight-chain alkyl or alkoxy groups, in each case having 2 to 10 carbon atoms. $Q^1$ and $Q^2$ are each 1,4-phenylene, trans-1,4-cyclohexylene, 4,4'-biphenylyl, 4-(trans-4-cyclohexyl)phenyl, trans,trans-4,4'-bicyclohexyl or one of the groups $Q^1$ and $Q^2$ is alternatively a single bond.

$Q^3$ and $Q^4$ are each 1,4-phenylene, 4,4'-biphenylyl or trans-1,4-cyclohexylene. One of the groups $Q^3$ and $Q^4$ may alternatively be 1,4-phenylene in which at least one CH group has been replaced by N. R''' is an optically active radical containing an asymmetric carbon atom of the structure

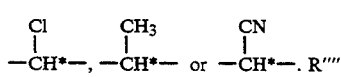

preferably has the formula

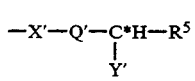

with the abovementioned preferred meanings.

Particularly preferred components having negative dielectric anisotropy are the compounds described in WO 86-00529 containing the structural element M or N. Particular preference is given to those of the formula IXd

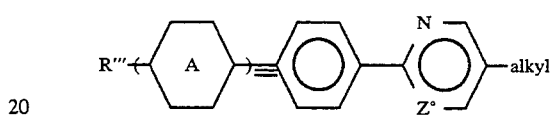

in which alkyl is a straight-chain or branched alkyl group, preferably having 3 to 10 carbon atoms, and R' is as defined above. Preference is also given to compounds conforming to the formula IXd in which one or two single bonds linking the rings have been replaced by a group selected from —$CH_2CH_2$—, —O—CO— or —CO—O—. Particularly preferred compounds of the formula VIc are those of the formula IXc':

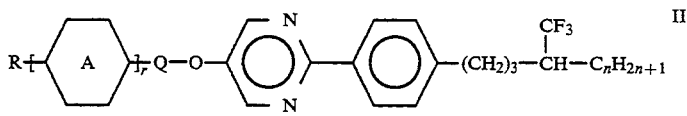

in which A is 1,4-phenylene or trans-1,4-cyclohexylene, Z° is CH or N, and n is 0 or 1.

Further preferred phases according to the invention contain, besides the compounds of the formula I, 2,5-disubstituted pyrimidines of the formula II

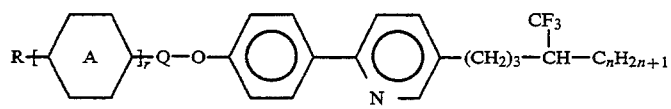

in which
R is alkyl, alkenyl or oxaalkyl having up to 12 carbon atoms,
A is trans-1,4-cyclohexylene, 1,4-phenylene or 1,3-cyclobutylene,
Q is —$CH_2$— or —CO—,
r is 0 or 1, and
n is 1 to 9, and/or
2,5-disubstituted heterocyclic compounds of the formula III

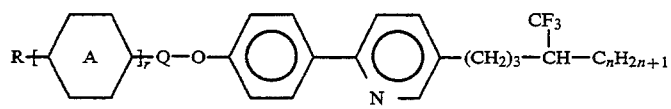

in which
R is alkyl, alkenyl or oxaalkyl having up to 12 carbon atoms,
A is trans-1,4-cyclohexylene, 1,4-phenylene or 1,3-cyclobutylene,
Q is —$CH_2$— or —CO—,
r is 0 or 1, and
n is 1 to 9.

The novel compounds of the formulae II and III have a broad range of applications. Depending on the choice of substituents, these compounds can be used as base materials of which liquid-crystalline phases are predominantly composed; however, it is also possible to add compounds of the formulae II and III to liquid-crystalline base materials from other classes of compound, in order, for example, to vary the dielectric and/or optical anisotropy and/or the spontaneous polarization and/or the phase range and/or the tilt angle and/or the pitch and/or the switching times of a phase of this type. The compounds of the formulae II and III are furthermore suitable as intermediates in the preparation of other substances which can be used as constituents of liquid-crystalline phases.

In the pure state, the compounds of the formulae II and III are colorless and have favorable optical anisotropy values. Some of the compounds of the formula I exhibit liquid-crystalline mesophases in a temperature range which is in a favorable position for electrooptical use, but isotropic or monotropically liquid-crystalline compounds of the formula [sic]II and III can also be employed advantageously as components of chiral tilted smectic phases. They are very stable chemically, thermally and to light.

The invention thus relates to the compounds of the formulae II and III, and to the use of the compounds of the formulae II and III as components of liquid-crystalline phases.

The invention also relates to chiral tilted smectic liquid-crystalline phases containing at least one compound of the formulae II and III.

The invention furthermore relates to electrooptical display elements which contain phases of this type.

Finally, the invention also relates to novel intermediates of the formula II'

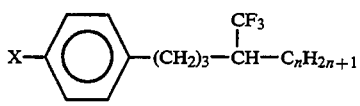

in which
n is 1 to 9,
$R^2$ is alkyl, alkenyl or oxaalkyl having up to 12 carbon atoms, and
X is cyano, carboxyl, amidine or hydroxymethyl, and the reactive derivatives thereof.

Above and below, R, A, Q, r and n are as defined for the compounds of the formulae II and III, unless expressly stated otherwise.

Compounds of the formulae above and below having branched wing groups R may be important. Branched groups of this type generally contain not more than two chain branches. R is preferably a straight-chain group or a branched group having not more than one chain branch.

Preferred branched radicals are isopropyl, 2-butyl (=1-methylpropyl), isobutyl (=2-methylpropyl), tert.-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

The radical R may also be an optically active organic radical containing an asymmetric carbon atom.

R is preferably alkyl or alkenyl having up to 12 carbon atoms. Particular preference is given to alkyl having 2 to 12 carbon atoms, ie. ethyl, propyl, butyl, pentyl, hexyl, heptyl, octyl, nonyl, decyl, undecyl and dodecyl. These groups may be straight-chain or branched, straight-chain alkyl groups being preferred. However, R is also preferably methyl or branched alkyl having a methyl branch, eg. isopropyl.

r is preferably 0.

The preferred compounds in which R is alkyl having up to 9 carbon atoms are preferably optically active and are used as chiral dopes for ferroelectric mixtures. The racemate can itself be used as a base material for mixtures of this type.

Of the compounds of the formulae II and III, those are preferred in which at least one of the radicals present therein has one of the preferred meanings indicated.

The compounds of the formulae II and III are prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for the reactions mentioned. Use may also be made here of variants which are known per se, but are not described here in greater detail.

If desired, the starting materials can also be formed in situ by not isolating them from the reaction mixture, but instead immediately reacting them further to give the compounds of the formulae II and III.

Thus, the compounds of the formula II or precursors which are suitable for their preparation can be prepared by reacting p-tolunitrile with 3-trifluoromethylalkyl iodides under basic conditions, which are themselves obtainable by the Finkelstein reaction (NaI/acetone) from the tosylates disclosed in EP-A-030 1511. An optically active 3-trifluoromethylalkyl iodide is preferably used.

The reaction conditions for the reaction of tolunitrile with the trifluoromethylalkyl iodides are not crucial per se. The metallation is carried out under the conditions given in DE 36 32 411 (Example 3) (where it may be possible to omit the use of DMPU), and an equimolar amount of optionally chiral trifluoromethylalkyl iodide is then added at −10° C.

The fluorocompounds of the formula II' (X=CN) according to the invention are obtained, from which the corresponding amidine hydrochloride is obtained by treatment with EtOH/HCl and $NH_3$.

The further synthesis of the compounds according to the invention is carried out in accordance with the following scheme:

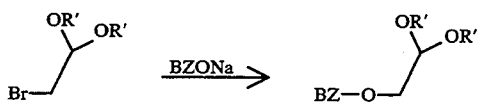

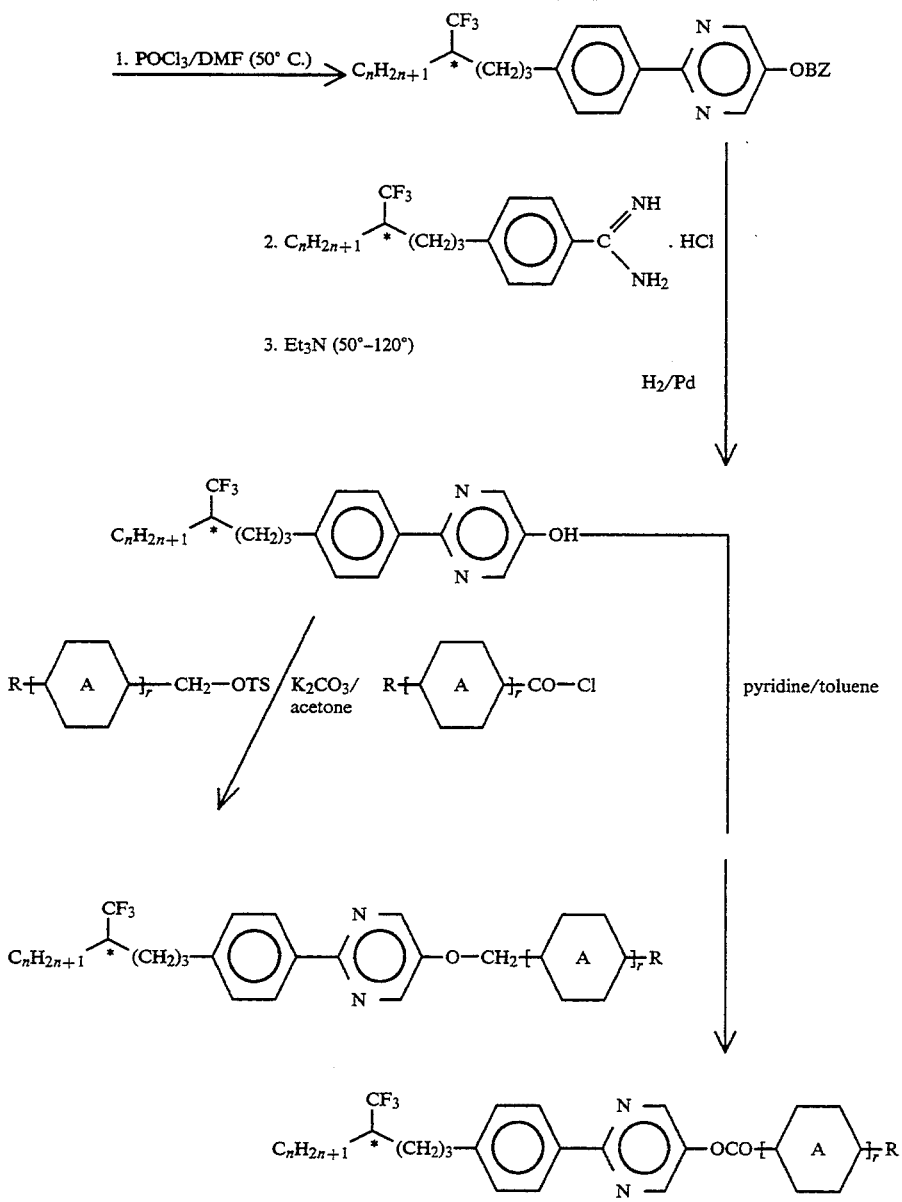

Thus, the compounds of the formula III or precursors which are suitable for their preparation can be prepared by reacting a compound of the formula III′

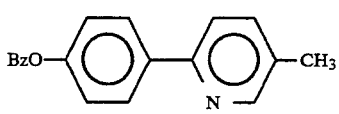

with a trifluoromethylalkyl iodide of the formula III″

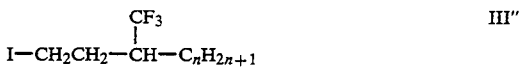

in which n is 1 to 9, under basic conditions. Preference is given to the use of an optically active compound II.

The reaction conditions for the reaction III′ with III″ are not crucial per se. The 2-substituted 5-methylpyridines of the formula I′ are metallated under the conditions given in DE 36 32 411 (Example 3) (where the use of DMPU may be omitted), and an equimolar amount of optionally chiral III″ is then added at −10° C.

The following scheme gives further details:

Scheme

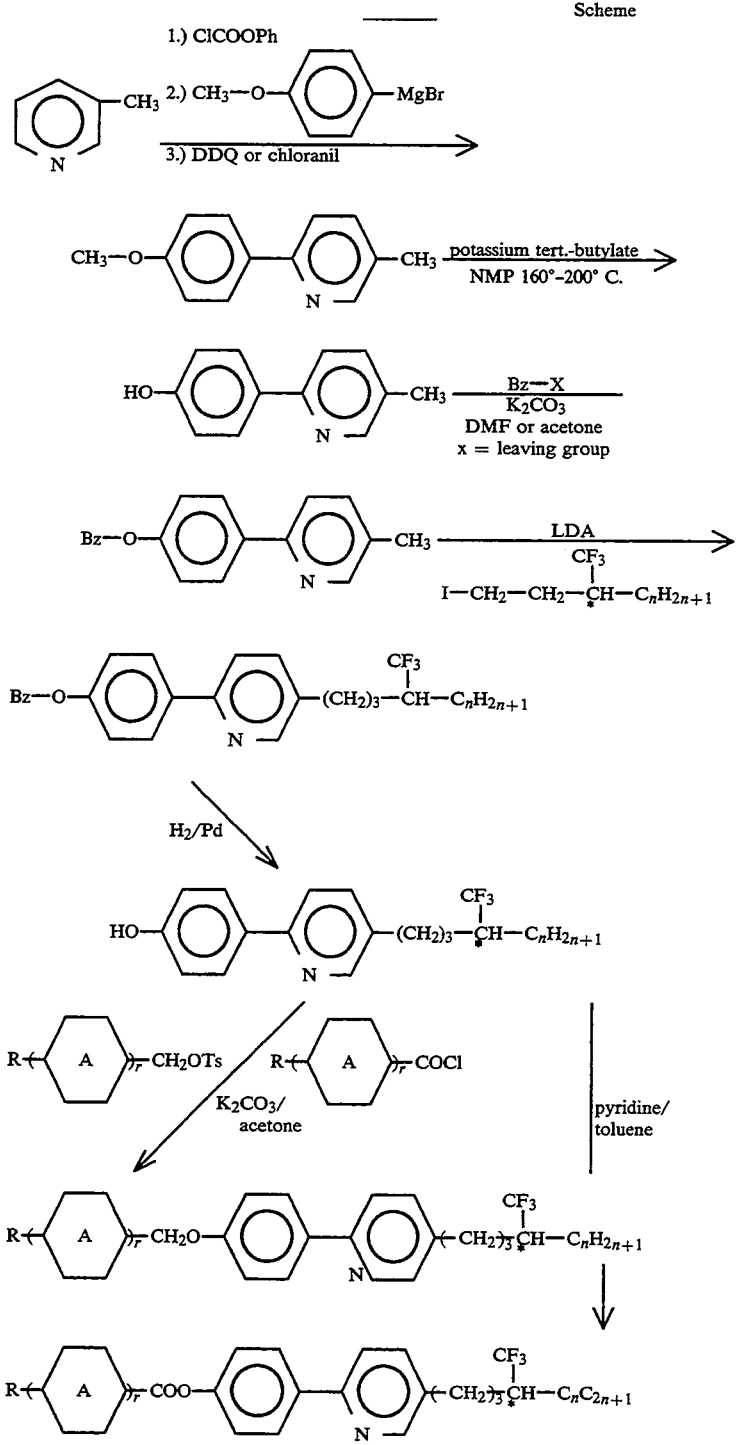

The starting materials of the formula III" are obtainable by the Finkelstein reaction (NaI acetone [sic]) from the corresponding tosylates disclosed in EP-A-0301511. The optically active tosylates are preferably employed. The starting materials of the formula III' are obtainable from 2-p-methoxyphenyl-5-methylpyridine by basic ether cleavage using K tert.-butylate in N-methylpyrrolidone (NMP) at 150°-200° C. and subsequent re-etherification using the appropriate benzyl halides or by cross-coupling the corresponding aromatic boric acids with 2-bromo-5-methylpyridine by the method of M. J. Sharp, W. Cheng and V. Snieckus, Tetrahedron Letters 28, 5093 (1987).

The compounds of the formulae I, II and III are also suitable as components of nematic liquid-crystalline phases, for example to avoid reverse twist.

These liquid-crystalline phases according to the invention comprise 2 to 25, preferably 3 to 15 components, including at least one compound of the formula I, II and/or III. The other constituents are preferably selected from nematic or nematogenic substances, in particular known substances from the classes comprising the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-biscyclohexylbiphenyls, phenyl- or cyclohexylpyrimidines, phenyl- or cyclohexylpyridazines and the N-oxides thereof, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolans and substituted cinnamic acids.

The most important compounds which are suitable as components of liquid-crystalline phases of this type can be characterized by the formula X

in which L and E are each a carbocyclic or heterocyclic ring system from the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline,
G is

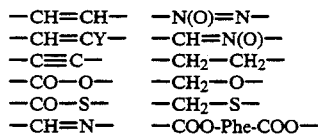

or a C-C single bond,
Y is halogen, preferably chlorine, or —CN, and R' and R'' are alkyl, alkoxy, alkanoyloxy, alkoxycarbonyl or alkoxycarbonyloxy having up to 18, preferably up to 8, carbon atoms, or one of these radicals is alternatively CN, NC, NO$_2$, —OCF$_3$, —OCF$_2$H, CF$_3$, F, Cl or Br.

In most of these compounds, R' and R'' are different from one another, one of these radicals usually being an alkyl or alkoxy group. However, other variants of the proposed substituents are also common. Many such substances or mixtures thereof are commercially available. All these substances can be obtained by methods which are known from the literature.

The phases according to the invention contain about 0.1 to 99, preferably 10 to 95%, of one or more compounds of the formula I. Additionally preferred liquid-crystalline phases according to the invention are those which contain 0.1–40, preferably 0.5–30%, of one or more compounds of the formula I.

The phases according to the invention are prepared in a manner which is customary per se. In general, the components are dissolved in one another, expediently at elevated temperature.

By means of suitable additives, the liquid-crystalline phases according to the invention can be modified in a manner such that they can be used in all types of liquid-crystal display elements which have been disclosed hitherto.

Additives of this type are known to those skilled in the art and are described in detail in the literature. For example, conductive salts, preferably ethyldimethyldodecylammonium 4-hexyloxybenzoate, tetrabutylammonium tetraphenylborate or complex salts of crown ethers (cf., for example, I. Haller et al., Mol. Cryst. Liq. Cryst. Volume 24, pages 249–258 (1973)) can be added in order to improve the conductivity, pleochroic dyes can be added to produce colored guest-host systems or substances can be added to modify the dielectric anisotropy, the viscosity and/or the orientation of the nematic phases.

Substances of this type are described, for example, in German Offenlegungsschrift 2,209,127, 2,240,864, 2,321,632, 2,338,281, 2,450,088, 2,637,430, 2,853,728 and 2,902,177.

The examples below are intended to illustrate the invention without representing a limitation. m.p.=melting point, c.p.=clear point. Above and below, percentages are percent by weight; all temperatures are given in degrees Celsius. "Customary work-up" means that water is added, the mixture is extracted with methylene chloride, the organic phase is separated off, dried and evaporated, and the product is purified by crystallization and/or chromatography.

In addition, the abbreviations have the following meanings:
C: crystalline solid state, S: smectic phase (the index denotes the phase type), N: nematic state, Ch: cholesteric phase, I: isotropic phase. The number between two symbols indicates the transition temperature in degrees Celsius.

EXAMPLE 1

0.05 mol of trans-4-(4'-octyloxybiphenyl-4-yl)cyclohexanecarbonyl chloride (prepared from 4-octyloxy-4'-bromobiphenyl by lithiation, conversion into an organotitanium compound and reaction with ethyl 4-cyclohexanonecarboxylate, dehydration and hydrogenation of the double bond, saponification of the ester and conversion of the acid using thionyl chloride), 0.05 mol of (S)-2-fluorooctanol and 0.05 mol of pyridine are refluxed for 5 hours in 100 ml of toluene. After the mixture has been cooled, the pyridine hydrochloride is filtered off with suction, and the filtrate is evaporated to give a residue.

The pure (S)-2-fluorooctyl [trans-4-(4'-octyloxybiphenyl-4-yl)cyclohexane]carboxylate is obtained by crystallization from ethanol.

EXAMPLE 2

0.1 mol of methyl 4-hydroxybenzoate, 0.1 mol of (S)-2-fluoro-1-octanol and 0.12 mol of triphenylphosphine are dissolved in 250 ml of tetrahydrofuran, and 0.12 mol of diethyl azodicarboxylate is added dropwise with stirring and ice cooling. The mixture is allowed to warm to room temperature, and is then stirred for a further 8 hours. The solvent is then distilled, and the methyl 4-(2-fluorooctyloxy)benzoate is purified by column chromatography. Saponification using aqueous/alcoholic potassium hydroxide solution gives (S)-4-(2-fluorooctyloxy)benzoic acid.

0.01 mol of this acid, 0,001 mol of 4-dimethylaminopyrimidine and 0.01 mol of 4-n-octylphenol are introduced into 15 ml of dichloromethane, a solution of 0.01 mol of dicyclohexylcarbodiimide is added dropwise at 10°with stirring, and the mixture is subsequently stirred at room temperature for a further 15 hours. The mixture is filtered through silica gel, and the solvent is evaporated to give, as the residue, (S)-(4-n-octylphenyl) 4-(2-fluorooctyloxy)benzoate.

EXAMPLE 3

(S)-4-(2-Fluorooctyloxy)benzoic acid and 2-(4-hydroxyphenyl)-5-n-nonylpyrimidine are reacted analogously to give (S)-[4-(5-n-nonylpyrimidin-2-yl)phenyl]4-(2-fluorooctyloxy)benzoate.

EXAMPLE 4

4-{5-[2-(4-pentylphenyl)ethynyl]pyrimidin-2-yl}benzoic acid is obtained in accordance with the following reaction scheme:

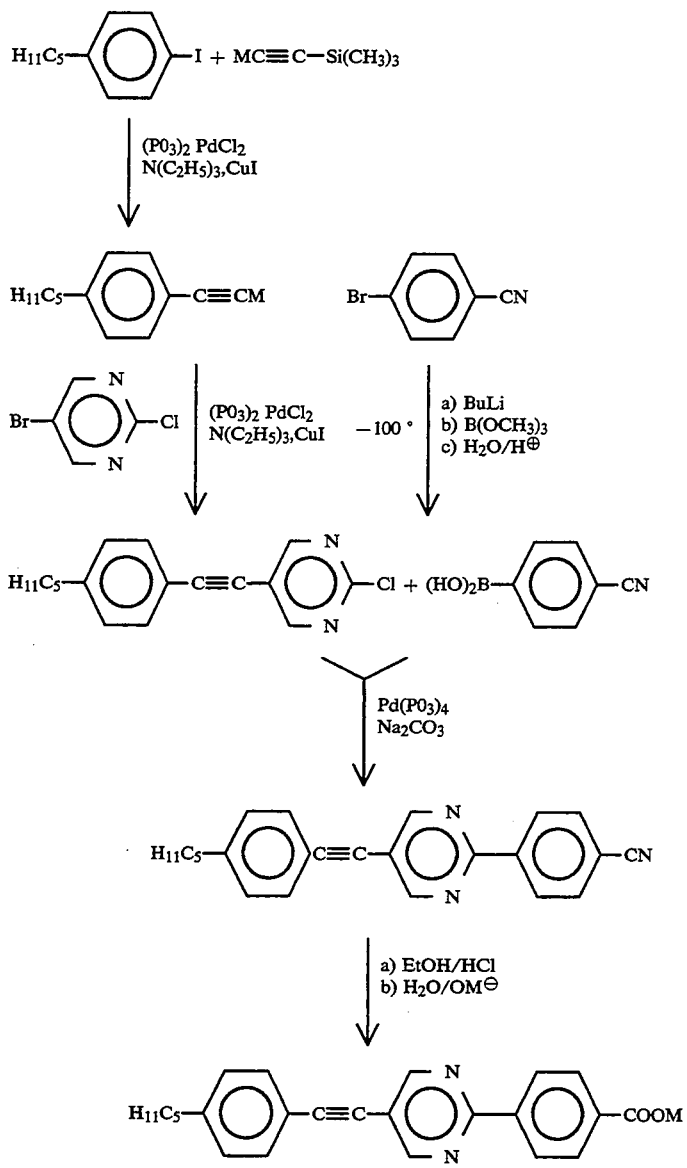

0.01 mol of this acid, 0.001 mol of dimethylaminopyridine and 0.01 mol of (S)-2-fluorooctanol are introduced into 15 ml of dichloromethane, a solution of 0.01 mol of dicyclohexylcarbodiimide is added dropwise at 10° with stirring, and the mixture is subsequently stirred at room temperature for a further 15 hours. The mixture is filtered through silica gel, and the solvent is evaporated to give, as the residue, (S)-2-fluorooctyl 4-{5-[2-(4-pentylphenyl)ethynyl]pyrimidin-2-yl}benzoate.

EXAMPLE 5

Hydrogenation of the compound obtained in Example 4 using hydrogen under atmospheric pressure at room temperature and using palladium/charcoal as catalyst gives (S)-2-fluorooctyl 4-{5-[2-(4-pentylphenyl)ethyl]-pyrimidin-2-yl}benzoate.

EXAMPLE 6

0.05 mol of (S)-4-(2-fluorooctyloxy)-4'-hydroxybiphenyl (prepared by alkylation of 4-hydroxy-4'-benzyloxybiphenyl using (S)-2-fluoro-1-octanol by the method of Mitsunobu and subsequent hydrogenolytic removal of the benzyl radical), 0.05 mol of trans-4-(3E-pentenyl)cyclohexanecarboxylic acid (preparation described in EP 0168683) and 0.005 mol of 4-dimethylaminopyridine are introduced into 75 ml of dichloromethane, a solution of 0.05 mol of dicyclohexylcarbodiimide is added dropwise at 10° with stirring, and the mixture is subsequently stirred at room temperature for a further 15 hours. Customary work-up gives (S)-[4-(2- fluorooctyloxy)biphenyl-4'-yl]trans-4-(3E-pentenyl)cyclohexane carboxylate.

EXAMPLE 7

0.02 mol of (S)-4-(2-fluorooctanoyloxy)-4'-hydroxybiphenyl (prepared by reaction of 4-benzoyloxy-4'-hydroxybiphenyl with (S)-2-fluorooctanoyl chloride in the presence of pyridine and subsequent removal of the benzyl group with hydrogenation), 0.02 mol of (S)-4-(2-fluorooctyloxy)benzoic acid and 0.002 mol of 4-dimethylaminopyridine are introduced into 30 ml of dichloromethane, a solution of 0.02 mol of dicyclohexylcarbodiimide is added dropwise at 10° with stirring, and the mixture is subsequently stirred at room temperature for a further 15 hours. Work-up gives (S,S)-[4-(2-fluorooctanoyloxy)-biphenyl-4'-yl] 4-(2-fluorooctyloxy)benzoate.

EXAMPLE 8

A solution of 0.1 mol of 5-heptyl-2-(4-2-hydroxy-5-oxaoctyloxy)phenyl)pyrimidine (prepared by heating optically active 1,2-epoxy-5-oxaoctane, obtainable from malic acid, with 5-heptyl-2-(p-hydroxyphenyl)pyrimidine in the presence of dry potassium carbonate and methyl ethyl ketone as solvent) in methyl chloride is cooled to −40° C., and 0.11 mol of DAST is added dropwise with exclusion of moisture. The reaction mixture is subsequently stirred at room temperature for 12 hours with slow warming, then hydrolyzed with ice cooling and washed with dilute sodium hydroxide solution and several times with water. After the mixture has been dried over magnesium sulfate, the solvent is removed on a rotary evaporator, and the crude product is purified by chromatography and crystallization, to give optically active 5-heptyl-2-(4-(2-fluoro-5-oxaoctyloxy)-phenyl)pyrimidine, C 41 $S_A$ (35) I.

The following is obtained analogously 5-heptyl-2-(4-(2-fluoro-4-oxadecyloxy)phenyl)pyrimidine, C 74 I

EXAMPLE 9

A solution of 0.11 mol of DCC in methylene chloride is added with ice cooling to a solution of optically active 2-fluoro-5-oxaoctanoic acid (obtainable by ring opening of optically active 1,2-epoxy-5-oxaoctane using pyridine/HF and oxidation of the alcohol to give the acid) and octyloxybiphenylol and a catalytic amount of DMAP in methylene chloride. The reaction mixture is stirred at room temperature for 12 hours, the precipitate is then removed by filtration, and the filtrate is subjected to customary work-up. The product is purified by crystallization and chromatography, to give optically active 4'-octyloxy-4-(2-fluoro-5-oxaoctanoyloxy)-biphenyl.

EXAMPLE 10

0.11 mol of DAST is added at −30° C. to a solution of 0.1 mol of 2-(p-octyloxyphenyl)-5-(3-hydroxy-6-oxanonyl)pyridine (obtainable by reaction of 2-(p-octyloxyphenyl)-5-methylpyridine with LDA at −40° C. and optically active 1,2-epoxy-5-oxaoctane) in methylene chloride, and the reaction mixture is then warmed slowly to room temperature. After 12 hours, the mixture is subjected to customary work-up, and the product is purified by crystallization, to give optically active 2-(p-octyloxyphenyl)-5-(3-fluoro-6-oxanonyl)pyridine.

EXAMPLE 11

A solution of 0.11 mol of DAST in methylene chloride is added dropwise at −40° C. with exclusion of moisture to a methylene chloride solution of 0.1 mol of the hydroxypyridine obtained by reacting 2-p-octyloxyphenyl-5-methylpyridine with optically active 1,2-epoxy-4-oxanonane in the presence of LDA. The reaction mixture is subsequently allowed to warm slowly to room temperature, and is then stirred for 12 hours. The reaction mixture is hydrolyzed, and the organic phase is washed with dilute sodium hydroxide solution and with water until neutral. The organic phase is dried using magnesium sulfate, the solvent is stripped off, and the residue is purified by crystallization and chromatography, to give optically active 2-(p-octyloxyphenyl)-5-(3-fluoro-5-oxadecyl)pyridine.

EXAMPLE 12

With exclusion of moisture and under an $N_2$ atmosphere, 70 ml of a solution of n-BuLi in hexane at about −40° C. are added to a solution of 90 ml of THF (tetrahydrofuran) and 15.6 ml of diisopropylamine, and 29.7 g of 2-p-octyloxyphenyl-5-methylpyridine dissolved in 100 ml of THF are then added at the same temperature. The reaction mixture is stirred at −10° C. for 30 minutes, and 2.8 g of optically active 3-fluoro-1-iodo-n-octane dissolved in 20 ml of THF are then added. The mixture is subsequently stirred at room temperature for 3 hours and then subjected to customary work-up, to give optically active 2-p-octyloxyphenyl-5-(4-fluorooctyl)pyridine.

The following are prepared analogously:
2-p-octyloxyphenyl-5-(4-fluoropentyl)pyridine
2-p-octyloxyphenyl-5-(4-fluorohexyl)pyridine
2-p-octyloxyphenyl-5-(4-fluoroheptyl)pyridine
2-p-octyloxyphenyl-5-(4-fluorooctyl)pyridine
2-p-octyloxyphenyl-5-(4-fluorodecyl)pyridine
2-p-octyloxyphenyl-5-(4-fluoroundecyl)pyridine
2-p-octyloxyphenyl-5-(4-fluorododecyl)pyridine 2-p-hexyloxyphenyl-5-(4-fluoropentyl)pyridine
2-p-hexyloxyphenyl-5-(4-fluorohexyl)pyridine
2-p-hexyloxyphenyl-5-(4-fluoroheptyl)pyridine
2-p-hexyloxyphenyl-5-(4-fluorooctyl)pyridine
2-p-hexyloxyphenyl-5-(4-fluorononyl)pyridine
2-p-hexyloxyphenyl-5-(4-fluorodecyl)pyridine
2-p-hexyloxyphenyl-5-(4-fluoroundecyl)pyridine
2-p-hexyloxyphenyl-5-(4-fluorododecyl)pyridine 2-p-heptyloxyphenyl-5-(4-fluoropentyl)pyridine
2-p-heptyloxyphenyl-5-(4-fluorohexyl)pyridine
2-p-heptyloxyphenyl-5-(4-fluoroheptyl)pyridine
2-p-heptyloxyphenyl-5-(4-fluorooctyl)pyridine
2-p-heptyloxyphenyl-5-(4-fluorononyl)pyridine
2-p-heptyloxyphenyl-5-(4-fluorodecyl)pyridine
2-p-heptyloxyphenyl-5-(4-fluoroundecyl)pyridine
2-p-heptyloxyphenyl-5-(4-fluorododecyl)pyridine 2-p-nonyloxyphenyl-5-(4-fluoropentyl)pyridine
2-p-nonyloxyphenyl-5-(4-fluorohexyl)pyridine
2-p-nonyloxyphenyl-5-(4-fluoroheptyl)pyridine
2-p-nonyloxyphenyl-5-(4-fluorooctyl)pyridine
2-p-nonyloxyphenyl-5-(4-fluorononyl)pyridine
2-p-nonyloxyphenyl-5-(4-fluorodecyl)pyridine
2-p-nonyloxyphenyl-5-(4-fluoroundecyl)pyridine
2-p-nonyloxyphenyl-5-(4-fluorododecyl)pyridine 2-p-decyloxyphenyl-5-(4- fluoropentyl)pyridine
2-p-decyloxyphenyl-5-(4- fluorohexyl)pyridine
2-p-decyloxyphenyl-5-(4- fluoroheptyl)pyridine
2-p-decyloxyphenyl-5-(4- fluorooctyl)pyridine
2-p-decyloxyphenyl-5-(4- fluorononyl)pyridine
2-p-decyloxyphenyl-5-(4- fluorodecyl)pyridine
2-p-decyloxyphenyl-5-(4- fluoroundecyl)pyridine
2-p-decyloxyphenyl-5-(4- fluorododecyl)pyridine 2-(3-fluoro-4-octyloxyphenyl-5-(4-fluoropentyl)pyridine
2-(3-fluoro-4-octyloxyphenyl-5-(4-fluorohexyl)pyridine
2-(3-fluoro-4-octyloxyphenyl-5-(4-fluoroheptyl)pyridine
2-(3-fluoro-4-octyloxyphenyl-5-(4-fluorononyl)pyridine
2-(3-fluoro-4-octyloxyphenyl-5-(4-fluorodecyl)pyridine
2-(3-fluoro-4-octyloxyphenyl-5-(4-fluoroundecyl)pyridine
2-(3-fluoro-4-octyloxyphenyl-5-(4-fluorododecyl)pyridine 2-(2,3-difluoro-4-octyloxyphenyl-5-(4-fluoropentyl)-pyridine
2-(2,3-difluoro-4-octyloxyphenyl-5-(4-fluorohexyl)pyridine
2-(2,3-difluoro-4-octyloxyphenyl-5-(4-fluoroheptyl)-pyridine
2-(2,3-difluoro-4-octyloxyphenyl-5-(4-fluorooctyl)pyridine
2-(2,3-difluoro-4-octyloxyphenyl-5-(4-fluorononyl)-pyridine
2-(2,3-difluoro-4-octyloxyphenyl-5-(4-fluorodecyl)pyridine
2-(2,3-difluoro-4-octyloxyphenyl-5-(4-fluoroundecyl)-pyridine
2-(2,3-difluoro-4-octyloxyphenyl-5-(4-fluorododecyl)-pyridine 2-p-heptyloxyphenyl-5-(3-fluoropentyl)pyridine
2-p-heptyloxyphenyl-5-(3-fluorohexyl)pyridine
2-p-heptyloxyphenyl-5-(3-fluoroheptyl)pyridine
2-p-heptyloxyphenyl-5-(3-fluorooctyl)pyridine
2-p-heptyloxyphenyl-5-(3-fluorononyl)pyridine, C 67 $S_B$ 71 $S_A$ 87 I
2-p-heptyloxyphenyl-5-(3-fluorodecyl)pyridine
2-p-heptyloxyphenyl-5-(3-fluoroundecyl)pyridine
2-p-heptyloxyphenyl-5-(3-fluorododecyl)pyridine 2-p-nonyloxyphenyl-5-(3-fluoropentyl)pyridine
2-p-nonyloxyphenyl-5-(3-fluorohexyl)pyridine
2-p-nonyloxyphenyl-5-(3-fluoroheptyl)pyridine
2-p-nonyloxyphenyl-5-(3-fluorooctyl)pyridine
2-p-nonyloxyphenyl-5-(3-fluorononyl)pyridine, C 73 $S_I$ 74 $S_c$ 87 $S_A$ 89 I
2-p-nonyloxyphenyl-5-(3-fluorodecyl)pyridine
2-p-nonyloxyphenyl-5-(3-fluoroundecyl)pyridine
2-p-nonyloxyphenyl-5-(3-fluorododecyl)pyridine 2-p-octyloxyphenyl-5-(3-fluoropentyl)pyridine
2-p-octyloxyphenyl-5-(3-fluorohexyl)pyridine
2-p-octyloxyphenyl-5-(3-fluoroheptyl)pyridine
2-p-octyloxyphenyl-5-(3-fluorooctyl)pyridine
2-p-octyloxyphenyl-5-(3-fluorononyl)pyridine, C 66 $S_I$ 73 $S_c$ 86 $S_A$ 90 I
2-p-octyloxyphenyl-5-(3-fluorodecyl)pyridine
2-p-octyloxyphenyl-5-(3-fluoroundecyl)pyridine
2-p-octyloxyphenyl-5-(3-fluorododecyl)pyridine

EXAMPLE 13

Preparation of 5-decyl-2-(p-(3-fluorodecyl-1-oxy)phenyl)pyrimidine.

With exclusion of moisture and with ice cooling, 0.1 mol of diethyl azodicarboxylate is added dropwise to a mixture of 0.1 mol of 5-decyl-2-p-hydroxyphenylpyrimidine, 0.105 mol of optically active 3-fluoro-1-decanol and 0.1 mol of triphenylphosphine in THF at such a rate that the reaction temperature 10° C. is not exceeded. The reaction mixture is subsequently allowed to warm slowly to room temperature, and is stirred for 48 hours. The solvent is then stripped off in vacuo, the residue is extracted with 3×100 ml of toluene, and the toluene phase is passed through a silica gel column. After the solvent has been evaporated, the product is purified by crystallization, C 56 $S_c$ 60 $S_A$ 70 I.

In a corresponding manner, 5-decyl-2-p-hydroxyphenylpyridine, 4-octyloxy-2,3-difluoro-4'-hydroxybiphenyl, 4-octyloxy-4'-hydroxy-2',4'-difluorobiphenyl and 4-octyloxy-4'-hydroxybiphenyl are etherified using optically active 3-fluoro-l-decanol by the method of Mitsunobu (Synthesis 1, 1981).

The following are obtained analogously:

5-undecyl-2-(4-(2-fluorooctyloxy)-2,3-difluorophenyl)-pyrimidine, K 60 $S_A$ (54) I 5-heptyl-2-(4-(2-fluorooctyloxy)-2,3-difluorophenyl)-pyrimidine, K 57 N (38) I 5-heptyl-2-(4-(2-fluorooctyloxy)phenyl-thia-3,4-diazole, C 109.0 I

EXAMPLE 14

0.2 mol of a 1.6 N solution of n-butyllithium in hexane and subsequently, at −30° C. to −40° C., a solution of 0.19 mol of 2 (p-octyloxyphenyl)-5-methylpyridine in THF are added to 0.2 mol of diisopropylamine in 100 ml of THF with exclusion of atmospheric oxygen and moisture. The reaction mixture is allowed to warm slowly until a clear solution is produced, and 0.2 mol of 3-trifluoromethylheptyl iodide (optically active) is then added. After 12 hours, the reaction mixture is hydrolyzed using saturated ammonium chloride solution, and is then subjected to customary work-up, giving optically active 2-(p-octyloxyphenyl)-5-(4-trifluoromethyloctyl)pyridine.

EXAMPLE 15

14.3 ml (0.185 mol) of DMF are added to 0.15 mol of POCl₃ with cooling at a maximum of 30°, and the mixture is stirred for 15 minutes. 22.5 g (0.1 mol) of 2-benzyloxyacetaldehyde diethyl acetal, dissolved in 50 ml of DMF, are added to the reaction solution. The reaction mixture is then heated at 50° C. for 12 hours, and p-(4-trifluoromethyloctyl)benzamidine [sic] hydrochloride (0.1 mol) is added in portions at room temperature. The mixture is stirred for 30 minutes, and 10 ml of triethylamine are then added. During this addition, the temperature increases to between 80° C. and 90° C. In order to keep the reaction mixture stirrable, DMF may be added. Some of the triethylamine is then removed by distillation at a maximum bath temperature of 160° C., the residue is allowed to cool to about 100° C., and 500 ml of water are then added, and the mixture is acidified using concentrated HCl. The precipitated crystals are filtered off with suction, washed thoroughly with water, dried and purified by chromatography. The benzyl group is subsequently removed by hydrogenation under atmospheric pressure using a Pd/C catalyst, and the hydroxyl group is alkylated under customary conditions:

0.1 mol of hydroxypyrimidine is dissolved in methyl ethyl ketone and refluxed for 24 hours together with 0.1 tool of 1-bromooctane in the presence of 0.15 mol of $K_2CO_3$. The mixture is then subjected to customary workup, to give optically active 2-p-(4-trifluoromethyloctyl)phenyl-5-octyloxypyrimidine.

EXAMPLE 16

4'-(4-r-cis-Cyano-4-heptylcyclohexyl)-4-(2-fluorooctyloxy)biphenyl 3.8 g of 4'-(4-r-cis-cyano-4-heptylcyclohexyl) -biphenyl-4-ol (obtainable from 4'-(4-r-cis-cyano-4-heptylcyclohexyl)-4-octyloxybiphenyl, prepared in accordance with DE 32 31 707, by basic ether cleavage using potassium tertiary-butylate in N-methylpyrrolidone at 180° C.), 1.5 g of optically active 2-fluorooctanol and 2.67 g of triphenylphosphorus [sic] are dissolved in 50 ml of THF. 1.59 ml of DEAD, dissolved in 10 ml of THF, are then added at about 10°–20° C. The mixture is subsequently stirred at room temperature for one hour, and the reaction mixture is then evaporated in vacuo. The residue is filtered with toluene through a frit covered by a layer of silica gel, and the filtrate is evaporated. Repeated recrystallization from ethyl acetate gives optically active 4'-(4-r-cis-cyano-4-heptylcyclohexyl)-4-(2-fluorooctyloxy)biphenyl, C 110 $S_A$ 159 I.

The examples below relate to liquid-crystalline media according to the invention:

Example A

A liquid-crystalline medium comprising
17.0% of 2-(p-heptyloxyphenyl)-5-nonylpyrimidine
17.0% of 2-(p-octyloxyphenyl)-5-nonylpyrimidine
17.0% of 2-(p-nonyloxyphenyl)-5-nonylpyrimidine
5.7% of 2-(4-heptyloxy-2,3-difluorophenyl)-5-nonylpyrimidine
5.7% of 2-(p-octyloxy-2,3-difluorophenyl)-5-nonylpyrimidine
5.7% of 2-(p-nonyloxy-2,3-difluorophenyl)-5-nonylpyrimidine
17.0% of 2-(p-hexyloxyphenyl)-5-hexyloxypyrimidine and
15% of optically active 4'-(2-fluorooctyloxy)-4-(4-r-cis-cyano-4-heptylcyclohexyl)biphenyl has $S^*_c$ 67 $S^*_A$ 72 Ch 78 I and a switching time of 35 μs at 20° C. and 15 V/μm

Example B

A liquid-crystal base mixture (B) comprising
3.3 % of 2-(p-hexyloxyphenyl)-5-heptylpyrimidine
3.3 % of 2-(p-heptyloxyphenyl)-5-heptylpyrimidine
3.3 % of 2-(p-octyloxyphenyl)-5-heptylpyrimidine
3.3 % of 2-(p-nonyloxyphenyl)-5-heptylpyrimidine
7.7 % of 2-(p-hexyloxyphenyl)-5-nonylpyrimidine
25.3 % of 2-(p-nonyloxyphenyl)-5-nonylpyrimidine
30.8 % of 4'-(4-r-cis-cyano-4-butylcyclohexyl)-4-octyloxybiphenyl
15.4 % of 4'-(4-r-cis-cyano-4-hexylcyclohexyl) -4-heptyl biphenyl and
6.6 % of r-1-cyano-cis-4-(trans-4-pentylcyclohexyl)-1-(trans-4-pentylcyclohexyl)cyclohexane has $S_c$ 76 $S_A$ 80 N 99 I.

This base mixture is doped with 10% of optically active 2-(p-2-fluorooctyloxyphenyl)-5-decylpyrimidine.

The doped mixture has the following physical properties:
phase transitions: $S^*_c$ 74 $S^*_A$ 80 Ch 94 I
spontaneous polarization (20° C.): 8.8 nC/cm$^2$
switching time (20° C., 15 Vμm$^{-1}$): 150 μs

Example C

The liquid-crystalline base mixture (B) (composition see Example B) is doped with 10% of optically active 2-(p-octyloxyphenyl)-5-(3-fluorononyl)pyridine.

The doped mixture has the following physical properties:
phase transitions
$S^*_c$ 76 $S^*_A$ 84 Ch 97 I
spontaneous polarization (20° C.): −11.3 nC/cm$^2$
switching time (20° C., 15 Vμm$^{-1}$): 150 μs

Example D

The liquid-crystalline base mixture (B) (composition see Example B) is doped with 10% of optically active 2-(4-(2-fluorooctyloxy)-2,3-difluorophenyl)-5-heptylpyrimidine.

The doped mixture has the following physical properties:
phase transitions:
$S^*_c$ 68 $S^*_A$ 71 Ch 92 I
spontaneous polarization (20° C.): 10.1 nC/cm$^2$
switching time (20° C., 15 Vμm$^{-1}$): 137 μs

Example E

The liquid-crystalline base mixture (B) (composition see Example B) is doped with 10% of optically active 2-(p-nonyloxyphenyl)-5-(3-fluorononyl)pyridine.

The doped mixture has the following physical properties:
phase transitions
$S^*_c$ 76 $S^*_A$ 84 Ch 96 I
spontaneous polarization (20° C.): 10.4 nC/cm$^2$
switching time (20° C., 15 Vμm$^{-1}$): 136 μs

Example F

The liquid-crystalline base mixture (B) (composition see Example B) is doped with 10% of optically active 2-(p-heptyloxyphenyl)-5-(3-fluorononyl)pyridine.

This mixture has the following physical properties:
phase transitions:
$S^*_c$ 74 $S^*_A$ 82 Ch 94 I spontaneous polarization (20° C.): 10.1 nC/cm$^2$

Example G

The liquid-crystalline base mixture (B) (composition see Example B) is doped with 10% of optically active 2-(4-(2-fluorooctyloxy)-2,3-difluorophenyl)-5-undecylpyrimidine.

The doped mixture has the following physical properties:
phase transitions
$S^*$72 $S^*_A$ 79 Ch 93 I
spontaneous polarization (20° C.): 19.0 nC/cm$^2$
switching time (20° C., 15 Vμm$^{-1}$): 218 μs

Example H

The liquid-crystalline base mixture (B) is doped with 10% of optically active 2-(p-(2-fluoro-5-oxaoctyloxy)-phenyl)-5-heptylpyrimidine.

The doped mixture has the following physical properties:
phase transitions
$S^*_c$ 70 $S^*_A$ 70.5 Ch 90 I

Example I

The liquid-crystalline base mixture (B) is doped with 10% of optically active 2-(p-(2-fluoro-4-oxadecyloxy)-phenyl)-5-heptylpyrimidine.

The doped mixture has the following physical properties:

phase transitions
$S^*_C$ 69 $S^*_A$ 73 Ch 91 I
spontaneous polarization (20° C.): 10.6 nC/cm$^2$
switching time (20° C., 15 V$\mu$m$^{-1}$): 140 $\mu$s

Example J

The liquid-crystalline base mixture (B) is doped with 10% of optically active 5-heptyl-2-(4-(2-fluorooctyloxy)phenyl)thia-3,4-diazole.

The doped mixture has the following physical properties:

phase transitions: $S^*_C$ 76 $S^*_A$ 84 Ch 97 I
spontaneous polarization (20° C.): 3.4 nC/cm$^2$
switching time (20° C., 15 V$\mu$m$^{-1}$): 140 $\mu$s

We claim:

1. An optically active compound of the formula

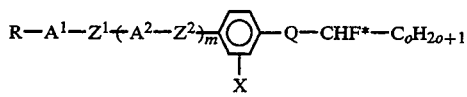

[IV]

wherein

R is a straight-chain alkyl or alkenyl radical having up to 15 carbon atoms, in which one CH$_2$ group is optionally replaced by —O—, —CO—, —O—CO—, —CO—O—, or —O—CO—O—;

A$^1$ and A$^2$ are each, independently of one another, a 1,4-phenylene radical, a pyridine-2,5-diyl radical, a pyrimidine-2,5-diyl radical, a pyrazine-2,5-diyl radical, a pyridazine-3,6-diyl radical, a 1,2,4-thiadiazole-3,5-diyl radical or a trans-1,4-cyclohexylene radical, each of which is unsubstituted or substituted by one or two fluorine atoms, and in which, in addition, one or two CH$_2$ groups are optionally replaced by —O— or —S—, and one CH group is optionally replaced by —C(CN)—, or are a 1,4-cyclohexenylene radical;

Z$^1$ and Z$^2$ are each, independently of one another, —O—CO—, —CH$_2$O—, —OCH$_2$—, —CH$_2$CH$_2$—, —CH=CH—, —C≡C—, or a single bond;

X is H or F;

Q is —OCH$_2$—, —COOCH$_2$—, or —CH$_2$OCH$_2$—;

O is 1 to 9;

m is 0 or 1, with the proviso that one of the rings A$^1$ and A$^2$ is trans-1,4-cyclohexylene in which one CH group has been replaced by —C(CN)—.

2. A chiral tilted smectic liquid-crystalline phase having at least two liquid-crystalline components wherein the phase contains at least one compound according to claim 1.

3. An electrooptical display element, containing a dielectric, wherein the dielectric is a phase according to claim 2.

* * * * *